United States Patent
Belardinelli et al.

(10) Patent No.: US 8,906,878 B2
(45) Date of Patent: *Dec. 9, 2014

(54) MYOCARDIAL PERFUSION IMAGING METHODS AND COMPOSITIONS

(71) Applicant: Gilead Sciences, Inc., Foster City, CA (US)

(72) Inventors: Luiz Belardinelli, Palo Alto, CA (US); Mitchell Rosner, Mountain View, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/848,614

(22) Filed: Mar. 21, 2013

(65) Prior Publication Data

US 2013/0343987 A1    Dec. 26, 2013

Related U.S. Application Data

(63) Continuation of application No. 13/361,775, filed on Jan. 30, 2012, now Pat. No. 8,470,801, which is a continuation of application No. 12/749,328, filed on Mar. 29, 2010, now Pat. No. 8,133,879, which is a continuation of application No. 10/766,403, filed on Jan. 27, 2004, now abandoned, which is a continuation-in-part of application No. 10/629,368, filed on Jul. 29, 2003, now Pat. No. 7,683,037.

(60) Provisional application No. 60/399,176, filed on Jul. 29, 2002, provisional application No. 60/399,177, filed on Jul. 29, 2002, provisional application No. 60/426,902, filed on Nov. 15, 2002, provisional application No. 60/459,803, filed on Apr. 2, 2003.

(51) Int. Cl.
| | | |
|---|---|---|
| A61K 31/70 | (2006.01) | |
| A61K 49/00 | (2006.01) | |
| A61K 31/7076 | (2006.01) | |
| A61K 51/00 | (2006.01) | |
| A61K 51/04 | (2006.01) | |

(52) U.S. Cl.
CPC .................. *A61K 51/00* (2013.01); *A61K 49/00* (2013.01); *A61K 31/7076* (2013.01); *A61K 51/0476* (2013.01); *A61K 51/0478* (2013.01)
USPC .......................................................... 514/46

(58) Field of Classification Search
CPC ... A61K 51/00; A61K 49/00; A61K 31/7076; A61K 51/0476; A61K 51/0478; A61K 2300/00
See application file for complete search history.

(56) References Cited

U.S. PATENT DOCUMENTS

| | | | |
|---|---|---|---|
| 3,845,770 | A | 11/1974 | Theeuwes et al. |
| 4,089,959 | A | 5/1978 | Diamond |
| 4,120,947 | A | 10/1978 | Diamond |
| 4,325,956 | A | 4/1982 | Kjellin et al. |
| 4,326,525 | A | 4/1982 | Swanson et al. |
| 4,593,095 | A | 6/1986 | Snyder et al. |
| 4,696,932 | A | 9/1987 | Jacobson et al. |
| 4,804,664 | A | 2/1989 | Kjellin et al. |
| 4,902,514 | A | 2/1990 | Barclay et al. |
| 4,956,345 | A | 9/1990 | Miyasaka et al. |
| 4,968,687 | A | 11/1990 | Findeisen et al. |
| 4,992,445 | A | 2/1991 | Lawter et al. |
| 5,001,139 | A | 3/1991 | Lawter et al. |
| 5,032,252 | A | 7/1991 | Owen et al. |
| 5,070,877 | A | 12/1991 | Mohiuddin et al. |
| 5,189,027 | A | 2/1993 | Miyashita et al. |
| 5,270,304 | A | 12/1993 | Kogi et al. |
| 5,459,254 | A | 10/1995 | Yamaguchi et al. |
| 5,516,894 | A | 5/1996 | Reppert |
| 5,593,975 | A | 1/1997 | Cristalli |
| 5,616,345 | A | 4/1997 | Geoghegan et al. |
| 5,641,784 | A | 6/1997 | Kufner-Muhl et al. |
| 5,646,156 | A | 7/1997 | Jacobson et al. |
| 5,670,498 | A | 9/1997 | Suzuki et al. |
| 5,703,085 | A | 12/1997 | Suzuki et al. |
| 5,704,491 | A | 1/1998 | Graves |
| 5,705,491 | A | 1/1998 | Yamada |
| 5,770,716 | A | 6/1998 | Khan et al. |
| 5,776,960 | A | 7/1998 | Oppong et al. |
| 5,780,481 | A | 7/1998 | Jacobson et al. |

(Continued)

FOREIGN PATENT DOCUMENTS

| | | |
|---|---|---|
| CA | 0965411 | 4/1975 |
| CA | 2064742 | 12/1991 |

(Continued)

OTHER PUBLICATIONS

Swinyard et al. (I), "Pharmaceutical Necessities," Chapter 66 in Remington's Pharmaceutical Sciences, 18th Ed., Gennaro et al. (eds.), 1990, Mack Publishing Co, Easton, PA, only pp. 1318-1319 supplied.*

(Continued)

*Primary Examiner* — Lawrence E Crane

(74) *Attorney, Agent, or Firm* — Sheppard Mullins Richter & Hampton LLP

(57) ABSTRACT

A myocardial imaging method that is accomplished by administering one or more adenosine $A_{2A}$ adenosine receptor agonist to a human undergoing myocardial imaging as well as pharmaceutical compositions comprising at least one $A_{2a}$ receptor agonist, at least one liquid carrier, and at least one co-solvent.

3 Claims, 17 Drawing Sheets

(56) References Cited

U.S. PATENT DOCUMENTS

| | | | |
|---|---|---|---|
| 5,854,081 A | 12/1998 | Linden et al. | |
| 5,877,180 A | 3/1999 | Linden et al. | |
| 5,939,543 A | 8/1999 | Morozumi et al. | |
| 6,026,317 A | 2/2000 | Verani | |
| 6,117,878 A | 9/2000 | Linden | |
| 6,214,807 B1 * | 4/2001 | Zablocki et al. | 514/46 |
| 6,294,522 B1 | 9/2001 | Zablocki et al. | |
| 6,322,771 B1 | 11/2001 | Linden et al. | |
| 6,368,573 B1 | 4/2002 | Leung | |
| 6,387,913 B1 | 5/2002 | Mustafa | |
| 6,403,567 B1 * | 6/2002 | Zablocki et al. | 514/46 |
| 6,448,235 B1 | 9/2002 | Linden et al. | |
| 6,514,949 B1 | 2/2003 | Linden et al. | |
| 6,552,023 B2 | 4/2003 | Zablocki et al. | |
| 6,599,283 B1 | 7/2003 | Marzilli et al. | |
| 6,605,597 B1 | 8/2003 | Zablocki et al. | |
| 6,642,210 B1 * | 11/2003 | Zablocki et al. | 514/46 |
| 6,670,334 B2 | 12/2003 | Linden et al. | |
| 6,677,336 B2 | 1/2004 | Zablocki et al. | |
| 6,770,634 B1 | 8/2004 | Zablocki et al. | |
| 6,806,270 B2 * | 10/2004 | Biaggioni et al. | 514/234.2 |
| 6,815,446 B1 * | 11/2004 | Biaggioni et al. | 514/263.2 |
| 6,825,349 B2 | 11/2004 | Kalla et al. | |
| 6,855,818 B2 * | 2/2005 | Zablocki et al. | 536/27.3 |
| 6,916,804 B2 | 7/2005 | Castelhano et al. | |
| 6,977,300 B2 | 12/2005 | Kalla et al. | |
| 6,995,148 B2 | 2/2006 | Jones et al. | |
| 7,109,180 B2 * | 9/2006 | Zablocki et al. | 514/46 |
| 7,109,203 B2 | 9/2006 | Hart et al. | |
| 7,125,993 B2 | 10/2006 | Elzein et al. | |
| 7,144,872 B2 * | 12/2006 | Zablocki et al. | 514/46 |
| 7,183,264 B2 * | 2/2007 | Zablocki et al. | 514/46 |
| 7,553,823 B2 | 6/2009 | Zablocki et al. | |
| 7,582,617 B2 * | 9/2009 | Belardinelli et al. | 514/46 |
| 7,655,636 B2 * | 2/2010 | Gordi et al. | 514/46 |
| 7,655,637 B2 * | 2/2010 | Zablocki et al. | 514/46 |
| 7,671,192 B2 | 3/2010 | Zablocki et al. | |
| 7,683,037 B2 * | 3/2010 | Belardinelli | 514/46 |
| 7,732,595 B2 | 6/2010 | Zablocki et al. | |
| 7,956,179 B2 | 6/2011 | Zablocki et al. | |
| 8,071,566 B2 * | 12/2011 | Belardinelli et al. | 514/46 |
| 8,106,029 B2 * | 1/2012 | Gordi et al. | 514/46 |
| 8,133,879 B2 * | 3/2012 | Belardinelli et al. | 514/46 |
| 8,183,226 B2 * | 5/2012 | Belardinelli | 514/46 |
| 8,278,435 B2 * | 10/2012 | Zablocki et al. | 536/27.11 |
| 8,470,801 B2 * | 6/2013 | Belardinelli et al. | 514/46 |
| 2002/0012946 A1 | 1/2002 | Belardinelli et al. | |
| 2003/0235555 A1 | 12/2003 | Shealey et al. | |
| 2004/0038928 A1 | 2/2004 | Zablocki et al. | |
| 2004/0064039 A1 | 4/2004 | Belardinelli | |
| 2004/0137533 A1 | 7/2004 | Belardinelli et al. | |
| 2005/0020915 A1 | 1/2005 | Belardinelli et al. | |
| 2006/0159621 A1 | 7/2006 | Barrett | |
| 2007/0265445 A1 | 11/2007 | Zablocki et al. | |
| 2007/0299089 A1 | 12/2007 | Belardinelli et al. | |
| 2008/0170990 A1 | 7/2008 | Lieu et al. | |
| 2008/0213165 A1 | 9/2008 | Lieu et al. | |
| 2008/0267861 A1 | 10/2008 | Lieu et al. | |
| 2009/0081120 A1 | 3/2009 | Lieu et al. | |
| 2009/0317331 A1 | 12/2009 | Belardinelli et al. | |
| 2010/0081810 A1 | 4/2010 | Zablocki et al. | |
| 2010/0086483 A1 | 4/2010 | Belardinelli et al. | |
| 2010/0160620 A1 | 6/2010 | Zablocki et al. | |
| 2010/0179313 A1 | 7/2010 | Zablocki et al. | |
| 2010/0272645 A1 | 10/2010 | Belardinelli | |
| 2013/0343987 A1 | 12/2013 | Belardinelli | |

FOREIGN PATENT DOCUMENTS

| | | |
|---|---|---|
| CA | 2377746 A1 | 12/2000 |
| EP | 0 354 638 | 2/1990 |
| EP | 0 386 683 | 9/1990 |
| JP | SHO 48-26038 | 8/1973 |
| JP | Hei 5 1993 9197 | 1/1993 |
| WO | WO 92/00297 | 1/1992 |
| WO | WO 92/12260 | 7/1992 |
| WO | WO 93/23401 | 11/1993 |
| WO | WO 93/25677 | 12/1993 |
| WO | WO 95/11681 | 5/1995 |
| WO | WO 98/52611 | 11/1998 |
| WO | WO 98/57651 | 12/1998 |
| WO | WO 99/63938 | 12/1999 |
| WO | WO 00/78778 | 12/2000 |
| WO | WO 00/78779 | 12/2000 |
| WO | WO 01/16134 | 8/2001 |
| WO | WO 01/62979 | 8/2001 |
| WO | WO 03/088978 | 10/2003 |
| WO | WO 2004/011010 | 2/2004 |
| WO | WO 2005/082379 | 9/2005 |
| WO | WO 2006/044856 | 4/2006 |
| WO | WO 2006/076698 | 7/2006 |
| WO | WO 2007/092372 | 8/2007 |
| WO | WO 2008/028140 | 3/2008 |
| WO | WO 2008/042796 | 4/2008 |
| WO | WO 2008/063712 | 5/2008 |
| WO | WO 2008/086096 | 7/2008 |
| WO | WO 2008/143667 | 11/2008 |
| WO | WO 2009/076580 | 6/2009 |
| WO | WO 2010/037122 | 4/2010 |

OTHER PUBLICATIONS

Swinyard et al. (II), "Pharmaceutical Necessities," Chapter 66 in Remington's Pharmaceutical Sciences, 18th Ed., Gennaro et al. (eds.), 1990, Mack Publishing Co, Easton, PA, pp. 1286-1329 supplied.*

Harvey, S. C., "Blood, Fluids, Electrolytes and Hematologic Drugs," Chapter 40 in Remington's Pharmaceutical Sciences, 18th Ed., Gennaro et al. (eds.), 1990, Mack Publishing Co, Easton, PA, only pp. 800 and 821 supplied.*

U.S. Appl. No. 10/896,766, filed Jul. 22, 2004, Biaggioni et al.

Bergmann et al., "Oxidation of Hypoxanthines, Bearing 8-Aryl or 8-Pyridyl Substituents, byBovine Milk Xanthine Oxidase,", Biochimica et Biophysica Acta, vol. 484, No. 2, pp. 275-289 (1977).

Birdsall et al., "Purine N-Oxides-XL the 3-Acyloxypurine 8-Substitution Reaction: Scope:Syntheses of 8-Substituted Xanthines and Guanines," Tetrahedron, vol. 27, pp. 5969-5978 (1971).

Blackburn et al., "Adenosine Mediates IL-13-Induced Inflammation and Remodeling in the Lung and interacts in an IL13-Adenosine Amplification Pathway," J. Clin. Invest. vol. 112, No. 3, pp. 332-344 (2003).

Bruns, "Adenosine Antagonism by Purines, Pteridines and Benzopteridines in Human Fibroblasts," Biochemical Pharmacology, vol. 30, No. 4, pp. 325-333 (1981).

Buckle et al., "Inhibition of Cyclic Nucleotide Phosphodiesterase by Derivatives of 1,3-Bis(cyclopropylmethyl)xanthine," J. Med. Chem., vol. 37, pp. 476-485 (1994).

Cerqueira, "The Future of Pharmacologic Stress: Selective A2A Adenosine Receptor Agonists," Am. J. Cardiol., vol. 94 (2A), pp. 33D-42D (2004).

Cline et al., "Coronary Artery Angiography Using Multislice Computed Tomography Images," Circulation, vol. 102, pp. 1589-1590, XP002564059 (2000).

Crimi et al., "Purine Derivatives in the Study of Allergic Inflammation in Respiratory Diseases," Allergy, vol. 52, No. 34, pp. 48-54 (1997).

Cristalli et al., "2-Alkynyl Derivatives of Adenosine 5'-N'ethyluronamide: Selective A2 Adenosine Receptor Agonists with Potent Inhibitory Activity on Platelet Aggregation," J. Med. Chem., vol. 37, pp. 1720-1726 (1994).

Cushley et al., "Inhaled Adenosine and Guanosine on Airway Resistance in Normal and Asthmatic Subjects," Br. J. Clin. Pharmacol, vol. 15, No. 2, pp. 161-165 (1983).

Dalpiaz et al., "De Novo Analysis of Receptor Binding Affinity Data of Xanthine Adenosine Receptor Antagonists," Arzneim-Forsch/Drug Res., vol. 45, No. 3, pp. 230-233 (1995).

Dhalla et al., "Tachycardia Caused by A2A Adenosine Receptor Agonists is Mediated by Direct Sympathoexcitation in Awake Rates," Journal of Pharmacology and Experimental Therapeutics, USA, vol. 316, No. 2, pp. 695-702, XP009073100 (2006).

(56) References Cited

OTHER PUBLICATIONS

Driver et al., "Adenosine in Bronchoalveolar Lavage Fluid in Asthma," Am. Rev. Respir. Dis., vol. 148, No. 1, pp. 91-97 (1993).
Elias et al., "Airway Remodeling in Asthma," The Journal of Clinical Investigation, vol. 104, No. 8, pp. 1001-1006 (1999).
Erickson et al., "1,3,8-Trisubstituted Xanthines. Effects of Substitution Pattern upon Adenosine Receptor A1/A2 Affinity", J. Med. Chem., vol. 34, pp. 1431-1435 (1991).
Feoktistov et al., "Adenosine A2B Receptors: A Novel Therapeutic Target in Asthma," Trends Pharmacol. Sci., vol. 19, pp. 148-153 (1998).
Feoktistov et al., "Hypoxia Modulates Adenosine Receptors in Human Endothelial and Smooth Muscle Cells Toward an A2B Angiogenic Phenotype," Hypertension, vol. 44, No. 5, pp. 649-654, Epub 2004, PMID: 15452028 [PubMed—indexed for MEDLINE] (2004).
Gao et al., "Novel Short-Acting A2A Adenosine Receptor Agonists for Coronary Vasodilation: Inverse Relationship between Affinity and Duration of Action of A2A Agonists," Journal of Pharmacology and Experimental Therapeutics, vol. 298, pp. 209-218 (2001).
Glover et al., "Characterization of a New, Highly Selective Adenosine A2A Receptor Agonist with Potential Use in Pharmacologic Stress Perfusion Imaging", Circulation, vol. 110, pp. I-311 (1999).
Glover et al., "Pharmacological Stress Thallium Scintigraphy with 2-cyclohexylmethylidenehydrazinoadenosine (WRC-0470)," Circulation, vol. 94, pp. 1726-1732 (1996).
Harvey, "Blood Fluids, Electrolytes and Hematologic Drugs," Chapter 40 in Remington's Pharmaceutical Sciences, 18th Ed., Gennaro et al., Mack Publishing Co., East, PA, only pp. 800 and 821 supplied (1990).
Hendel et al. "Initial Clinical Experience with Regadenoson, a Novel Selective A2A Agonist for Pharmacologic Stress Single-Photon Emission Computed Tomography Myocardial Perfusion Imaging", Journal of the American College of Cardiology, vol. 46, No. 11, pp. 2069-2075 (2005).
Hendel et al., "Pharmacologic Stress SPECT Myocardial Perfusion Imaging with a Selective A2A Agonist: Results of a Pilot Study Comparing Adenosine with CVT-3146", Circulation, Supplement IV, vol. 108, pp. 2892 (2003).
Holgate et al., "Roles of Cysteinyl Leukotrienes in Airway Inflammation, Smooth Muscle Function and Remodeling," J. Allergy Clin. Imunol. (Suppl):S18-34; discussion S34-6, Review, PMID:12532084 [PubMed—indexed for MEDLINE] (2003).
Hoshino, "Impact of Inhaled Corticosteriods and Leukotrience Receptor Antagonists on Airway Remodeling," Clinical Reviews in Allergy & Immunology, vol. 27, No. 1, pp. 59-64 (2004).
Iskandrian, "Adenosine Myocardial Perfusion Imaging," The Journal of Nuclear Medicine, vol. 35, pp. 734-736 (1994).
Jacobson et al., "1,3-Dialkylxanthine Derivatives Having High Potency as Antagonists at HumanA2B Adenosine Receptors," Drug Development Research, vol. 47, pp. 45-53 (1999).
Jadbabaie et al., "Myocardial perfusion imaging with a novel selective A2A Adenosine Receptor Agonists (CVT-3146): Important differences in radiotracer behavior," Journal of Am. Col. Cardiology, vol. 41, pp. 443-444 (2003).
Jeffery, "Remodeling in Asthma and Chronic Obstructive Lung Disease," Am. J. Respir. Crit. Care Med., vol. 164, No. 10pt2, pp. S28-S38 (2001).
Katsushima et al., "Structure-Activity Relationships of 8-Cycloalkyl-1,3-dipropylxanthines as Antagonist of Adenosine Receptors," J. Med. Chem., vol. 33, pp. 1906-1910 (1990).
Kerensky et al. "Dose Dependent Increase in Human Coronary Blood Flow Velocity Following an IV Bolus of CVT-3146, A Novel A2A Adenosine Receptor Agonists: A Potential Agent for the Use in Pharmacological Stress Testing for Myocardial Perfusion Imaging", Circulation, Supplemental II, vol. 106, vol. 19, p. II-618, (2002).

Kim et al., "Acyl-Hydrazide Derivatives of a Xanthine Carboxylic Congener (XCC) as Selective Antagonists at Human A2B Adenosine Receptors", Drug Development Research, vol. 47, pp. 178-188 (1999).
Kleiner, "Reactions of Some 8-(3-Pyridyl)-6-thioxanthines with Methyl Iodide," pp. 739-743 (1973).
Klotz et al., "Comparative pharmacology of human adenosine receptors subtypes-characterization of stably transfected receptors in CHO cells," Nauny-Schmideberg's Arch Pharmacol., vol. 357, pp. 1-9 (1998).
Koepfli et al., "Interaction of caffeine with regadenoson-induced hyperemic myocardial blood flow as measured by PET", European Heart Journal, vol. 27, No. Supp. 1, p. 175, (2006).
Korolkovas, Essentials of Molecular Pharmacology—Background for Drug Design, Wiley—Interscience, New York, NY, only pp. 266-272 supplied, (1970).
Kubo et al., "Effect of Caffeine Intake on Myocardial Hyperemic Flow Induced by Adenosine Triphosphate and Dipyridamole," The Journal of Nuclear Medicine, vol. 45, No. 5, pp. 730-738, (2004).
Kusmic et al., "Coronary microcirculatory vasoconstriction induced by low-flow ischemia in mouse hearts is reversed by an A2A adenosine receptor", FASEB Journal, pp. A1227-A1228 (2007).
Leigh et al., "Is Interleukin-1 3 Critical in Maintaining Airway Hyperresponsiveness in Allergen-Challenged Mice?" Am. J. Respir. Crit. Care Med., PMID: 15242841 [PubMed—indexed for MEDLINE] vol. 170, No. 8, pp. 851-856 (2004).
Linden et al., "Characterization of Human A2B Adenosine Receptors: Radioligand Binding, WesternBlotting and Coupling to Gq in Human Embryonic Kidney 293 Cells and HMC-1 Mast Cells, " Molecular Pharacology, vol. 56, pp. 705-713 (1999).
Mager et al., "Molecular Simulation Applied to 2-(N'-alkylidenehydrazino)-and 2-(N'-aralkylidenehydrazino) adenosine A2 Agonists," European Journal of Medicinal Chemistry, vol. 30, pp. 15-25 (1995).
Mann et al., "Airway Effects of Purine Nucleosides and Nucleotides and Release With Bronchial Provocation in Asthma," J. Appl. Physiol., vol. 61, No. 5, pp. 1667-1676 (1986).
Martin et al., "Pharmacology of 2-cylohexylmethylidenehydrazionoadenosine (WRC-0470), a novel, short-acting adenosine A-2A receptor agonist that produces selective coronary vasodilation", Drug Development Research, vol. 40, No. 4, pp. 313-324, (1997).
Martinson et al., "Potent Adenosine Receptor Antagonists that are Selective for the A1 Receptor Subtype," Molecular Pharmacology, vol. 31, No. 3, pp. 247-252 (1986).
Marumoto et al. (I), "Synthesis and Coronary Vasodilating Activity of 2-Substituted Adenosines," Chemical Pharmaceutical Bulletin, vol. 23, No. 4, pp. 759-774 (1975).
Marumoto et al. (II), "Synthesis and Enzymatic Activity of Adenosine 3',5'-Cyclic Phosphate Analogues," Chemical Pharmaceutical Bulletin, vol. 27, No. 4, pp. 990-1003 (1979).
Matsuda et al., "Nucleosides and Nucleotides, 103. 2-Alkynyladenoines: A Novel Class of Selective Adenosine A2 Receptor Agonists with Potent Antihypertensive Effects," Journal of Medicinal Chemistry, vol. 35, No. 1, pp. 241-252 (1992).
Mosselhi et al., "Reactions of some 8-diazoxanthine derivatives", Indian Journal of Chemistry, vol. 33B, pp. 236-242 (1994).
Niiya et al., "2-(N'-Alkylidenehydrazino) Adenosines; Potent and Selective Coronary vasodilators," Journal of Medicinal Chemistry, American Chemical Society, vol. 35, No. 24, pp. 4557-4561, (1992).
Ogden, et al., Mean Body Weight, Height, and Body Mass Index, United States 1960-2002, U.S. National Health and Nutrition Examination Survey, Advance Data No. 347, pp. 1-18, (2004).
Persson et al., "Synthesis and Antiviral Effects of 2-Heteroaryl Substituted Adenosine and 8-Heteroaryl Guanosine Derivatives," Bioorganic & Medicinal Chemistry, vol. 3, No. 10, pp. 1377-1382 (1995).
Pfizer, "Health info.", (2003), http://www.pfizer.be/English/What_we_do_/Health_info/COPD.htm.
Pifferi et al., "Montelukast and Airway Remodeling in Children with Chronic Persistent Asthma: An Open Study," Pediatric Allergy and Immunology, vol. 15, No. 5, pp. L472-L473 (2004).

(56) References Cited

OTHER PUBLICATIONS

Polosa et al., "Evolving Concepts on the Value of Adenosine Hyperresponsiveness in Asthma and Chronic Obstructive Pulmonary Disease". Thorax, vol. 57, No. 7, pp. 649-654 (2002).

Polosa, "Adenosine-Receptor Subtypes: The Relevance to Adenosine-Mediated Responses in Asthma and Chronic Obstructive Pulmonary Disease," The European Respiratory Journal: Official Journal of the European Society for Clinical Respiratory Physiology., vol. 20, No. 2, pp. 488-496 (2002).

Riou et al., "Influence of propranolol, enalaprilat, verapamil, and caffeine on adenosine A(2A) receptor medicated coronary vasodilation", Journal of the American College of Cardiology, vol. 40, No. 9, pp. 1687-1690 (2002).

Roth et al., "8-Dicyclopropylmethylyl)-1,3-dipropylxanthine: A Potent and Selective Adenosine A1 Antagonist with Renal Protective and Diuretic Activities," J. Med. Chem., vol. 34, No. 1, pp. 466-469 (1991).

Ryzhov et al., "Adenosine-Activated Mast Cells Induce IgE Synthesis by B Lymphocytes: An A2B-Mediated Process Involving the Cytokines IL-4 and IL-13 with Implications for Asthma," vol. 172, No. 12, pp. 7726-7733, PMID: 15187156 [PubMed—indexed for MEDLINE] (2004).

Sambuceti et al., Coronary Vasoconstriction During Myocardial Ischemia Induced by Rises in Metabolic Demand in Patients with Cornary Artery Disease, Circulation, 1997; 95; (2652-2659) pp. 1-24.

Sambuceti et al., Interaction Between Coronary Artery Stenosis and Coronary Microcirculcation in Ishcemic Heart Disease, Z Kardiol, 2000; 89 Suppl 9:IX/126-31, abstract.

Shimada et al., "8-Polycycloalkyl-I,3-dipropylxanthines as Potent and Selective Antagonists forA1-Adenosine Receptors," J. Med. Chem., vol. 35, pp. 924-930 (1992).

Shryock et al., "A2A-Adenosine reserve for coronary vasodilation," Circulation 98:711-718 (1998).

Spicuzza et al., "Research Applications and Implications of Adenosine in Diseased Airways," Trends Pharmacol. Sci., vol. 24, No. 8, pp. 409-413, Review, PMID: 12915050 [Pubmed—indexed for MEDLINE] (2003).

Spicuzza et al., "The Role of Adenosine as a Novel Bronchoprovocant in Asthma," Curr. Opin. Allergy Clin. Immunol., vol. 3, No. 1, pp. 65-69 (2003).

Swinyard et al., "Pharmaceutical Necessities," Chapter 66 in Remington's Pharmaceutical Sciences, 18th Ed., Gennaro et al. (eds.), Mack Publishing Co, Easton, PA, only pp. 1318-1319 supplied (1990).

Swinyard et al., "Pharmaceutical Necessities," Chapter 66 in Remington's Pharmaceutical Sciences, 18th Ed., Gennaro et al. (eds.), Mack Publishing Co, Easton, PA, only pp. 1286-1329 supplied (1990).

Tomita et al., Artificial Neural Network Approach for Selection of Susceptible single Nucleotide Polymorphisms and Construction of Prediction Model on Childhood allergic Asthma: BMC Bioinformatics, vol. 1, No. 5, p. 120, PMID: 15339344 [PubMed—indexed for MEDLINE] (2004).

Trochu et al., "Selective A2A Adenosine Receptor Agonist as a Coronary Vasodilator in Conscious Dogs: Potential for Use in Myocardial Perfusion Imaging," Journal of Cardiovascular, vol. 41, No. 1, pp. 132-139 (2003).

Udelson et al., "Randomized, Controlled Dose-Ranging Study of the Selective Adenosine A2A Receptor Agonist Binodenoson for Pharmacological Stress as an Adjunct to Myocardial Perfusion Imaging," Circulation, vol. 209, pp. 457-464 (2004).

Van Der Wenden et al., "Mapping the Xanthine C8-region of the adenosine Al Receptor with Computer Graphics," European Journal of Pharmacology—Molecular Pharmacology Section,vol. 206, No. 1, pp. 315-323 (1991).

Xu et al., Coronary Vasodilation by a Short Acting, Low Affinity A2A Adenosine Receptor Agonist in Anesthetize Closed Chest Dogs: A Second Generation of Coronary Artery Pharmacologic Stressor, Circulation, vol. 102, No. 18, p. 3912 (2000).

Zablocki et al. 2-Substituted PI System Derivatives of Adenosine That are Coronary Vasodilators Acting via the A2A Adenosine Receptor, 2001, Nucleosides, Nucleotides and Nucleic Acids, 20: (4-7), pp. 343-360.

Zhao et al., "Caffeine attenuates the duration of coronary vasodilation and changes in hemodynamics induced by regadenoson (CVT-3146), a novel adenosine A2A receptor agonist," Journal of Cardiovascular Pharmacology, Raven Press, New York, NY, vol. 49, No. 6, pp. 369-375, XP009094871 (2007).

Zhao et al., "Comparative Profile of Vasodilation by CVT-3146, a novel A2A receptor agonist and adenosine in conscious dogs," Journal of Pharm & Experimental Therapeutics, Journal of Pharm. & Experimental Therapeutics, vol. 41, pp. 182-189 (2003).

Zhao et al., "Effects of caffeine on coronary vasodilation and sinue tachycardia induced by Regadenoson, a novel adenosine A2A receptor agonist, in conscious dogs," European Heart Journal, vol. 27, No. Suppl. 1, p. 424 (2006).

Zhao et al., "Regadenoson, a novel pharmacologic stress agent for use in myocardial perfusion imaging, does not have a direct effect on the QT interval in conscious dogs," Journal of Cardio Vascular Pharmacology, pp. 467-473, vol. 52, No. 5, Lippincott Williams and Wilkins, USA, XP8117431 (2008).

Zhong et al., "Synergy Between A2B Adenosine Receptors and Hypoxia in Activating Human Lung Fibroblasts," American Journal of Respiratory Cell and Molecular Biology, vol. 32, No. 1, pp. 2-8 (2005).

Office Action for U.S. Appl. No. 11/766,964, dated Apr. 7, 2011, 16 pages.

Office Action for U.S. Appl. No. 11/864,437, dated Mar. 29, 2011, 12 pages.

Office Action for U.S. Appl. No. 11/969,047, dated Mar. 17, 2011, 13 pages.

Office Action for U.S. Appl. No. 12/435,176, dated Apr. 15, 2011, 12 pages.

Office Action for U.S. Appl. No. 12/637,583, dated Apr. 4, 2011, 10 pages.

Office Action for U.S. Appl. No. 12/695,096, dated Apr. 14, 2011, 8 pages.

Office Action for U.S. Appl. No. 12/765,623, dated Mar. 8, 2011, 7 pages.

Final Office Action for U.S. Appl. No. 12/749,328 dated Jun. 8, 2011, 17 pages.

Office Action for U.S. Appl. No. 12/749,328 dated Oct. 7, 2010, 18 pages.

Final Office Action for U.S. Appl. No. 12/695,096, dated Oct. 5, 2011, 6 pages.

Office Action for U.S. Appl. No. 13/361,775 dated Jul. 25, 2012, 8 pages.

* cited by examiner

CVT-3146 and Coronary Flow Velocity
*Duration of Effect:*

| Dose (n) | Duration ≥2.5 Baseline Mean ± SEM |
|---|---|
| 10 μg (4) | 0 |
| 30 μg (4) | 0 |
| 100 μg (3) | 0.2 ± 0.2 minutes |
| 300 μg (4) | 2.2 ± 1.3 minutes |
| 400 μg (8) | 2.8 ± 0.8 minutes |
| 500 μg (4) | 2.9 ± 1.3 minutes |

Figure 3

All Drug-Related Adverse Events Were Mild and Transient

| Adverse Event | All Doses (n = 36) | 400 µg (n = 9) |
|---|---|---|
| chest discomfort | 3 | 3 |
| increased heart rate | 3 | 1 |
| hypotension | 2 | 2 |
| flushing | 2 | 1 |
| shortness of breath | 2 | 0 |
| funny taste in mouth | 1 | 0 |
| sensation in mouth, sinus, and chest | 1 | 0 |
| headache | 1 | 1 |
| tingling in hands | 1 | 1 |
| heart racing | 1 | 1 |
| bradycardia | 1 | 1 |
| lightheadedness | 1 | 1 |
| cough | 1 | 0 |
| nausea and vomiting | 1 | 0 |

Figure 7

MYOCARDIAL PERFUSION IMAGING METHODS AND COMPOSITIONS

This application is a continuation of U.S. patent application Ser. No. 13/361,775, filed on Jan. 30, 2012, now U.S. Pat. No. 8,470,801, which is a continuation of U.S. patent application Ser. No. 12/749,328, filed on Mar. 29, 2010, now U.S. Pat. No. 8,133,879, which is a continuation of U.S. patent application Ser. No. 10/766,403, filed on Jan. 27, 2004, now abandoned, which is a continuation-in-part of U.S. patent application Ser. No. 10/629,368, filed on Jul. 29, 2003, now U.S. Pat. No. 7,683,037, which claims the benefit of U.S. Provisional Patent Application No. 60/459,803 filed on Apr. 2, 2003, and U.S. Provisional Patent Application No. 60/426,902 filed on Nov. 15, 2002, and U.S. Provisional Patent Application No. 60/399,177 filed on Jul. 29, 2002, and U.S. Provisional Patent Application No. 60/399,176 filed on Jul. 29, 2002 which are hereby incorporated by reference in their entirety.

BACKGROUND OF THE INVENTION (1) Field of the Invention

This invention relates to myocardial imaging methods that are accomplished by administering doses of one or more adenosine $A_{2A}$ adenosine receptor agonists to a mammal undergoing myocardial imaging. This invention also relates to pharmaceutical compositions useful in myocardial imaging methods.

(2) Description of the Art

Myocardial perfusion imaging (MPI) is a diagnostic technique useful for the detection and characterization of coronary artery disease. Perfusion imaging uses materials such as radionuclides to identify areas of insufficient blood flow. In MPI, blood flow is measured at rest, and the result compared with the blood flow measured during exercise on a treadmill (cardiac stress testing), such exertion being necessary to stimulate blood flow. Unfortunately, many patients are unable to exercise at levels necessary to provide sufficient blood flow, due to medical conditions such as peripheral vascular disease, arthritis, and the like.

Therefore, a pharmacological agent that increases cardiac blood flow (CBF) for a short period of time would be of great benefit, particularly one that did not cause peripheral vasodilation. Vasodilators, for example dipyridamole, have been used for this purpose in patients prior to imaging with radionuclide. Dipyridamole is an effective vasodilator, but side effects such as pain and nausea limit the usefulness of treatment with this compound.

Adenosine, a naturally occurring nucleoside, also is useful as a vasodilator. Adenosine exerts its biological effects by interacting with a family of adenosine receptors characterized as subtypes $A_1$, $A_{2A}$, $A_{2B}$, and $A_3$. Adenoscan® (Fujisawa Healthcare Inc.) is a formulation of a naturally occurring adenosine. Adenoscan® has been marketed as an adjuvant in perfusion studies using radioactive thallium-201. However, its use is limited due to side effects such as flushing, chest discomfort, the urge to breathe deeply, headache, throat, neck, and jaw pain. These adverse effects of adenosine are due to the activation of other adenosine receptor subtypes other than $A_{2A}$, which mediates the vasodilatory effects of adenosine. Additionally, the short half-life of adenosine necessitates multiple treatments during the procedure, further limiting its use. Adenoscan® is contraindicated in many patients including those with second- or third-degree block, sinus node disease, bronchoconstrictive or bronchospastic lung disease, and in patients with known hypersensitivity to the drug.

Other potent and selective agonists for the $A_{2A}$ adenosine receptor are known. For example, MRE-0470 (Medco) is an adenosine $A_{2A}$ receptor agonist that is a potent and selective derivative of adenosine. WRC-0470 (Medco) is an adenosine $A_{2A}$ agonist used as an adjuvant in imaging. In general, compounds such as these have a high affinity for the $A_{2A}$ receptor, and consequently, a long duration of action, which is undesirable in imaging.

Thus, there is still a need for a method of producing rapid and maximal coronary vasodilation in mammals without causing corresponding peripheral vasodilation, which would be useful for myocardial imaging with radionuclide agents. Preferred compounds would be selective for the $A_{2A}$ adenosine receptor and have a short duration of action (although longer acting than compounds such as adenosine), thus obviating the need for multiple dosing.

SUMMARY OF THE INVENTION

The following are several aspects of this invention.

A method of producing coronary vasodilation without peripheral vasodilation in a human, comprising administering at least 10 μg of at least one $A_{2A}$ receptor agonist to the human.

A method of producing coronary vasodilation without peripheral vasodilation in a human, comprising administering no more than about 1000 μg of a $A_{2A}$ receptor agonist to the human.

A method of producing coronary vasodilation without peripheral vasodilation in a human, comprising administering a $A_{2A}$ receptor agonist in an amount ranging from about 10 to about 600 μg to the human.

A method of producing coronary vasodilation without peripheral vasodilation in a human, comprising administering about 300 μg of a $A_{2A}$ receptor agonist to the human.

A method of producing coronary vasodilation without peripheral vasodilation in a human, comprising administering about 400 μg of a $A_{2A}$ receptor agonist to the human.

A method of producing coronary vasodilation without peripheral vasodilation in a human, comprising administering about 500 μg of a $A_{2A}$ receptor agonist to the human.

A method of producing coronary vasodilation without peripheral vasodilation in a human, comprising administering about 600 μg of a $A_{2A}$ receptor agonist to the human.

A method of producing coronary vasodilation without peripheral vasodilation in a human, comprising administering about 700 μg of a $A_{2A}$ receptor agonist to the human.

A method of myocardial perfusion imaging of a human, comprising administering a radionuclide and a $A_{2A}$ receptor agonist wherein the $A_{2A}$ receptor agonist is administered in an amount ranging from about 10 to about 600 μg and wherein the $A_{2A}$ receptor agonist is administered in a single dose.

A method of myocardial perfusion imaging of a human, comprising administering a radionuclide and a $A_{2A}$ receptor agonist wherein about 300 μg of the $A_{2A}$ receptor agonist is administered in a single dose.

A method of myocardial perfusion imaging of a human, comprising administering a radionuclide and a $A_{2A}$ receptor agonist wherein about 400 μg of the $A_{2A}$ receptor agonist is administered in a single dose.

A method of myocardial perfusion imaging of a human, comprising administering a radionuclide and a $A_{2A}$ receptor agonist wherein about 500 μg of the $A_{2A}$ receptor agonist is administered in a single dose.

A method of myocardial perfusion imaging of a human, comprising administering a radionuclide and a $A_{2A}$ receptor agonist wherein about 600 µg of the $A_{2A}$ receptor agonist is administered in a single dose.

A method of myocardial perfusion imaging of a human, comprising administering a radionuclide and a $A_{2A}$ receptor agonist wherein about 700 µg of the $A_{2A}$ receptor agonist is administered in a single dose.

A method of myocardial perfusion imaging of a human, comprising administering a radionuclide and a $A_{2A}$ receptor agonist wherein the $A_{2A}$ receptor agonist is administered in an amount ranging from about 10 to about 600 µg and wherein the $A_{2A}$ receptor agonist is administered by iv bolus.

A method of myocardial perfusion imaging of a human, comprising administering a radionuclide and a $A_{2A}$ receptor agonist wherein the $A_{2A}$ receptor agonist is administered in an amount ranging from about 0.05 to about 60 µg/kg and wherein the $A_{2A}$ receptor agonist is administered by iv bolus.

A method of myocardial perfusion imaging of a human, comprising administering a radionuclide and a $A_{2A}$ receptor agonist wherein the $A_{2A}$ receptor agonist is administered in an amount ranging from about 0.1 to about 30 µg/kg wherein the $A_{2A}$ receptor agonist is administered by iv bolus.

A method of myocardial perfusion imaging of a human, comprising administering a radionuclide and a $A_{2A}$ receptor agonist wherein the $A_{2A}$ receptor agonist is administered in an amount no greater than about 20 µg/kg to a supine patient wherein the $A_{2A}$ receptor agonist is administered by iv bolus.

A method of myocardial perfusion imaging of a human, comprising administering a radionuclide and a $A_{2A}$ receptor agonist wherein the $A_{2A}$ receptor agonist is administered in an amount no greater than about 10 µg/kg to a standing patient wherein the $A_{2A}$ receptor agonist is administered by iv bolus.

A method of myocardial perfusion imaging of a human, comprising administering a radionuclide and a $A_{2A}$ receptor agonist wherein the $A_{2A}$ receptor agonist is administered in an amount ranging from about 10 to about 600 µg wherein the $A_{2A}$ receptor agonist is administered in about 20 seconds.

A method of myocardial perfusion imaging of a human, comprising administering a radionuclide and a $A_{2A}$ receptor agonist in an amount ranging from about 10 to about 600 µg wherein the $A_{2A}$ receptor agonist is administered in less than about 10 seconds.

A method of myocardial perfusion imaging of a human, comprising administering a radionuclide and a $A_{2A}$ receptor agonist wherein the $A_{2A}$ receptor agonist is administered in an amount greater than about 10 µg.

A method of myocardial perfusion imaging of a human, comprising administering a radionuclide and a $A_{2A}$ receptor agonist wherein the $A_{2A}$ receptor agonist is administered in an amount greater than about 100 µg.

A method of myocardial perfusion imaging of a human, comprising administering a radionuclide and an $A_{2A}$ receptor agonist wherein the $A_{2A}$ receptor agonist is administered in an amount no greater than about 600 µg.

A method of myocardial perfusion imaging of a human, comprising administering a radionuclide and an $A_{2A}$ receptor agonist wherein the $A_{2A}$ receptor agonist is administered in an amount no greater than about 500 µg.

A method of myocardial perfusion imaging of a human, comprising administering a radionuclide and a $A_{2A}$ receptor agonist wherein the $A_{2A}$ receptor agonist is administered in an amount ranging from about 100 µg to about 500 µg and preferably about 400 µg.

A method of myocardial perfusion imaging of a human, comprising administering a radionuclide and an $A_{2A}$ receptor agonist wherein the $A_{2A}$ receptor agonist is selected from the group consisting of CVT-3033, CVT-3146 and combinations thereof.

A method of myocardial perfusion imaging of a human, comprising administering a radionuclide and about 300 µg of a compound selected from the group consisting of CVT-3033 and CVT-3146 to the human.

A method of myocardial perfusion imaging of a human, comprising administering a radionuclide and about 400 µg of a compound selected from the group consisting of CVT-3033 and CVT-3146 to the human.

A method of myocardial perfusion imaging of a human, comprising administering a radionuclide and about 500 µg of a compound selected from the group consisting of CVT-3033 and CVT-3146 to the human.

A method of myocardial perfusion imaging of a human, comprising administering a radionuclide and about 600 µg of a compound selected from the group consisting of CVT-3033 and CVT-3146 to the human.

A method of myocardial perfusion imaging of a human, comprising administering a radionuclide and about 700 µg of a compound selected from the group consisting of CVT-3033 and CVT-3146 to the human.

A method of myocardial perfusion imaging of a human, comprising administering a radionuclide and a $A_{2A}$ receptor agonist wherein the human's myocardium is examined for areas of insufficient blood flow following administration of the radionuclide and the $A_{2A}$ receptor agonist.

A method of myocardial perfusion imaging of a human, comprising administering a radionuclide and a $A_{2A}$ receptor agonist wherein the myocardium is examined for areas of insufficient blood flow following administration of the radionuclide and the $A_{2A}$ receptor agonist wherein the myocardium examination begins within about 1 minute from the time the $A_{2A}$ receptor agonist is administered.

A method of myocardial perfusion imaging of a human, comprising administering a radionuclide and an $A_{2A}$ receptor agonist wherein the administration of the $A_{2A}$ receptor agonist causes at least a 2.5 fold increase in coronary blood flow.

A method of myocardial perfusion imaging of a human, comprising administering a radionuclide and a $A_{2A}$ receptor agonist wherein the administration of the $A_{2A}$ receptor agonist causes at least a 2.5 fold increase in coronary blood flow that is achieved within about 1 minute from the administration of the $A_{2A}$ receptor agonist.

A method of myocardial perfusion imaging of a human, comprising administering a radionuclide and an $A_{2A}$ receptor agonist wherein the radionuclide and the $A_{2A}$ receptor agonist are administered separately.

A method of myocardial perfusion imaging of a human, comprising administering a radionuclide and an $A_{2A}$ receptor agonist wherein the radionuclide and the $A_{2A}$ receptor agonist are administered simultaneously.

A method of myocardial perfusion imaging of a human, comprising administering a radionuclide and a $A_{2A}$ receptor agonist wherein the administration of the $A_{2A}$ receptor agonist causes at least a 2.5 fold increase in coronary blood flow for less than about 5 minutes.

A method of myocardial perfusion imaging of a human, comprising administering a radionuclide and a $A_{2A}$ receptor agonist wherein the administration of the $A_{2A}$ receptor agonist causes at least a 2.5 fold increase in coronary blood flow for less than about 3 minutes.

A method of myocardial perfusion imaging of a human, comprising administering CVT-3146 in an amount ranging from about 10 to about 600 µg in a single iv bolus.

A method of myocardial perfusion imaging of a human, comprising administering CVT-3146 in an amount ranging from about 100 to about 500 µg and more preferably about 400 µg in a single iv bolus.

A method of myocardial perfusion imaging of a human comprising administering CVT-3146 by iv bolus in an amount ranging from 10 to about 600 µg that is independent of the weight of the human being dosed.

Pharmaceutical compositions comprising at least one $A_{2A}$ receptor agonist, at least one liquid carrier, and at least one co-solvent.

Pharmaceutical compositions comprising at least one $A_{2A}$ receptor agonist, at least one liquid carrier, and at least one co-solvent wherein the $A_{2A}$ receptor agonist is selected from the group consisting of CVT-3033, CVT-3146, and combinations thereof.

Pharmaceutical compositions comprising at least one $A_{2A}$ receptor agonist, at least one liquid carrier, and at least one co-solvent wherein the liquid carrier comprises water, distilled water, de-ionized water, saline, a buffer, or combinations thereof.

Pharmaceutical compositions comprising at least one $A_{2A}$ receptor agonist, at least one liquid carrier, and at least one co-solvent wherein the co-solvent comprises methylboronic acid, borate buffer, propylene glycol, or polyethylene glycol.

Pharmaceutical compositions comprising at least one $A_{2A}$ receptor agonist, at least one liquid carrier, and at least one co-solvent wherein the co-solvent is methylboronic acid.

Pharmaceutical compositions comprising at least one $A_{2A}$ receptor agonist, at least one liquid carrier, and at least one co-solvent wherein the co-solvent is methylboronic acid and wherein the $A_{2A}$ receptor agonist is CVT-3146.

Pharmaceutical compositions comprising CVT-3146, at least one liquid carrier, and at least one co-solvent wherein the co-solvent is methylboronic acid wherein the CVT-3146 is present in an amount ranging from about 50 micrograms/ml to about 250 micrograms/ml and the methylboronic acid is present in an amount from about 0.4% to about 0.6% (w:v).

Pharmaceutical compositions comprising CVT-3146, at least one liquid carrier, and at least one co-solvent wherein the co-solvent is methylboronic acid having a pH of from about 9.1 to about 9.4.

Pharmaceutical compositions comprising at least one $A_{2A}$ receptor agonist, at least one liquid carrier, and at least one co-solvent wherein the co-solvent is a borate buffer and preferably about 0.5% (w:v) methylboronic acid.

Pharmaceutical compositions comprising at least one $A_{2A}$ receptor agonist, at least one liquid carrier, and at least one co-solvent wherein a co-solvent is a borate buffer and preferably about 0.5% (w:v) methylboronic acid and wherein the composition further comprises a buffer to bring the pH of the composition to about 9.3.

Pharmaceutical compositions comprising at least one $A_{2A}$ receptor agonist, at least one liquid carrier, and at least one co-solvent wherein the co-solvent is a borate buffer and wherein the $A_{2A}$ receptor agonist is CVT-3146 which is preferably present in the composition in an amount from about 50 to about 150 micrograms/ml.

Pharmaceutical compositions comprising at least one $A_{2A}$ receptor agonist, at least one liquid carrier, and at least one co-solvent wherein the co-solvent is a borate buffer, wherein the $A_{2A}$ receptor agonist is CVT-3146 which is preferably present in the composition in an amount from about 50 to about 150 micrograms/ml and wherein said composition also comprises about 0.55% (w:v) sodium chloride and about 50 mM sodium bicarbonate.

Pharmaceutical compositions comprising at least one $A_{2A}$ receptor agonist, at least one liquid carrier, and at least one co-solvent wherein the co-solvent is propylene glycol and the propylene glycol is present in an amount of from about 5% to about 25% (w:v) and preferably in an amount of from about 8% to about 20% (w:v).

Pharmaceutical compositions comprising at least one $A_{2A}$ receptor agonist, at least one liquid carrier, and at least one co-solvent wherein the co-solvent is propylene glycol and the propylene glycol is present in an amount of from about 5% to about 25% (w:v) wherein the liquid carrier includes a buffer to bring said composition to a pH of from about 6 to about 8.

Pharmaceutical compositions comprising at least one $A_{2A}$ receptor agonist, at least one liquid carrier, and at least one co-solvent wherein the co-solvent is propylene glycol and the propylene glycol is present in an amount of from about 5% to about 25% wherein said composition further comprises EDTA.

Pharmaceutical compositions comprising at least one $A_{2A}$ receptor agonist, at least one liquid carrier, and at least one co-solvent wherein the co-solvent is propylene glycol and the propylene glycol is present in an amount of from about 5% to about 25% (w:v) and preferably in an amount of from about 8% to about 20% (w:v) wherein the $A_{2A}$ receptor agonist is CVT-3146 and said CVT-3146 is present in an amount from about 50 to about 150 micrograms.

A method of producing coronary vasodilation without peripheral vasodilation comprising administering to a human the pharmaceutical composition comprising at least one $A_{2A}$ receptor agonist, at least one liquid carrier, and at least one co-solvent.

A method of producing coronary vasodilation without peripheral vasodilation comprising administering to a human the pharmaceutical composition comprising at least one $A_{2A}$ receptor agonist, at least one liquid carrier, and at least one co-solvent wherein the $A_{2A}$ receptor agonist is CVT-3146.

A method of producing coronary vasodilation without peripheral vasodilation comprising administering to a human the pharmaceutical composition comprising at least one $A_{2A}$ receptor agonist, at least one liquid carrier, and at least one co-solvent wherein the $A_{2A}$ receptor agonist is CVT-3146 and wherein said pharmaceutical composition is administered by iv bolus.

A method of producing coronary vasodilation without peripheral vasodilation comprising administering to a human the pharmaceutical composition comprising at least one $A_{2A}$ receptor agonist, at least one liquid carrier, and at least one co-solvent wherein the $A_{2A}$ receptor agonist is CVT-3146 and wherein said pharmaceutical composition is administered by iv bolus and wherein said pharmaceutical composition is administered in about 10 to about 20 seconds.

A method of producing coronary vasodilation without peripheral vasodilation comprising administering to a human the pharmaceutical composition comprising at least one $A_{2A}$ receptor agonist, at least one liquid carrier, and at least one co-solvent wherein the $A_{2A}$ receptor agonist is CVT-3146 wherein the total amount of CVT-3146 that is administered ranges from about 100 to about 500 micrograms and is more preferably about 400 micrograms.

In all of the methods above, the dose is preferably administered in a single dose.

In all of the methods above, at least one radionuclide is administered before, with or after the administration of the $A_{2A}$ receptor agonist to facilitate myocardial imaging.

In all of the methods above, the dose is preferably administered in 60 seconds or less, preferably 30 seconds or less, and more preferably 20 seconds or less.

DESCRIPTION OF THE FIGURES

FIG. 3 is a Table that reports the duration of time the coronary flow velocity is greater than or equal to 2.5 times baseline coronary flow velocity for varying doses of CVT-3146 wherein "n" refers to the number of human patients dosed;

FIG. 7 is an adverse event Table;

DESCRIPTION OF THE INVENTION

Figure 1:
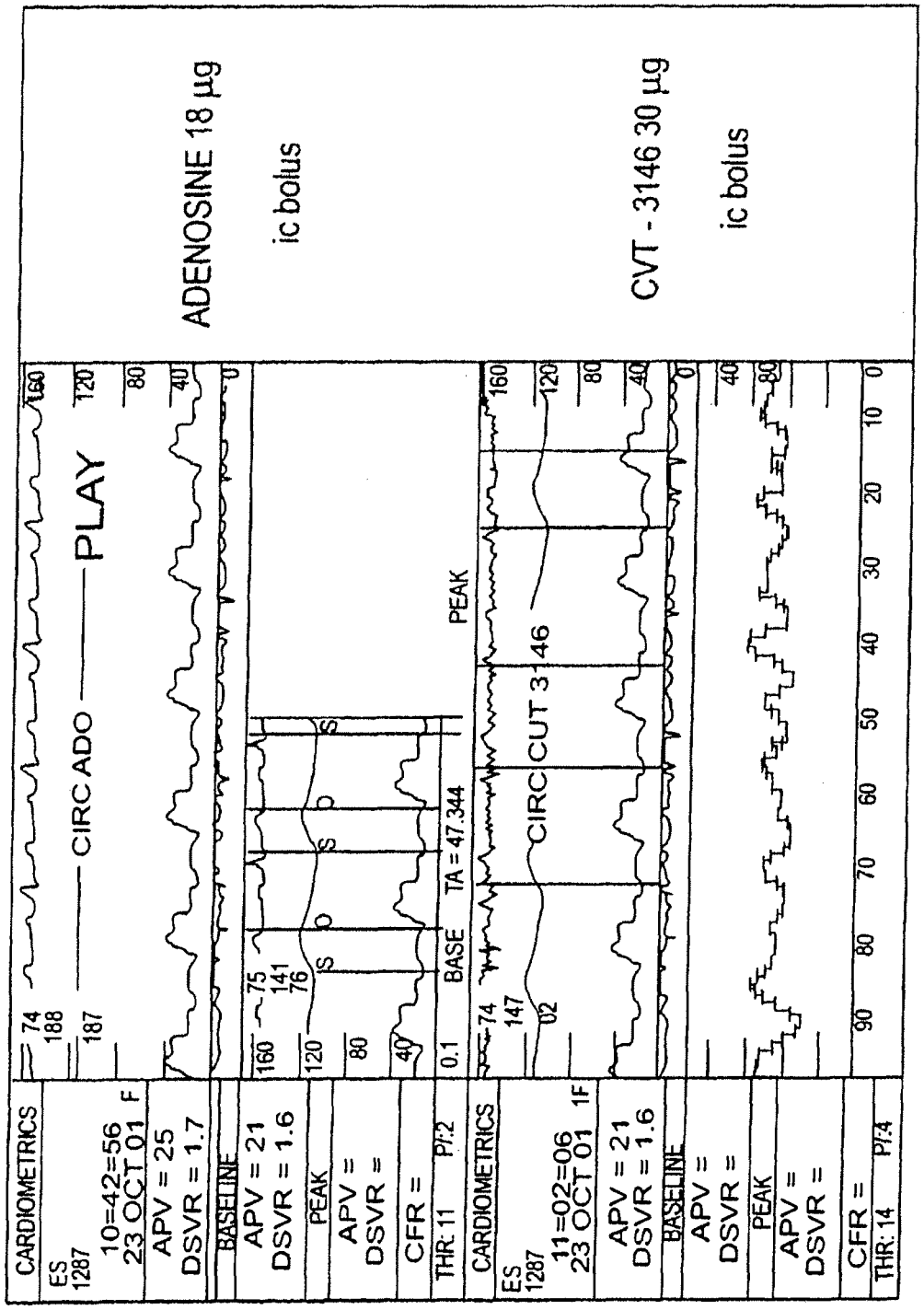
FIG. 1 are intracoronary Doppler flow profiles following administration of 18 μg adenosine IC bolus (top) and 30 μg CVT-3146 IV bolus.
Figure 2:
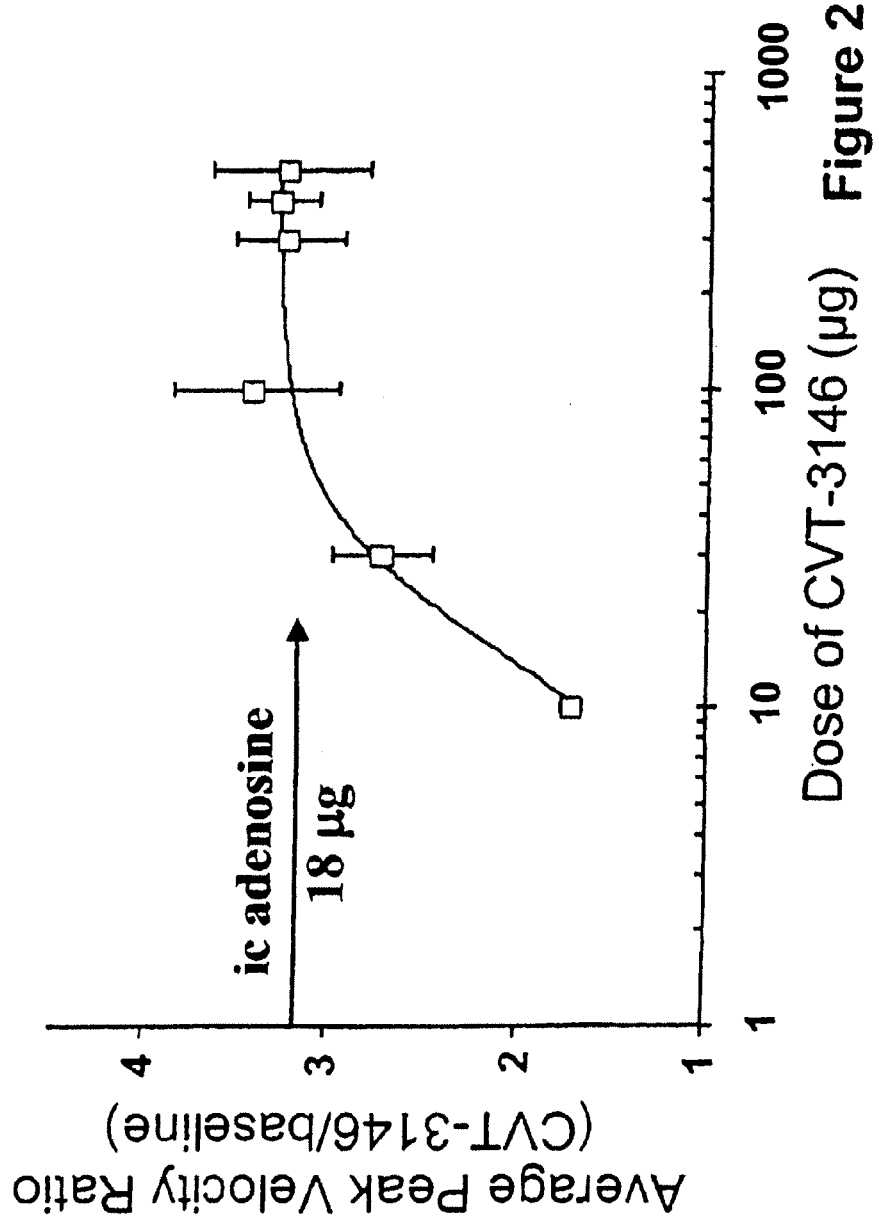
FIG. 2 is a plot showing the relationship of the dose of CVT-3146 on coronary peak flow rates.
Figure 4:
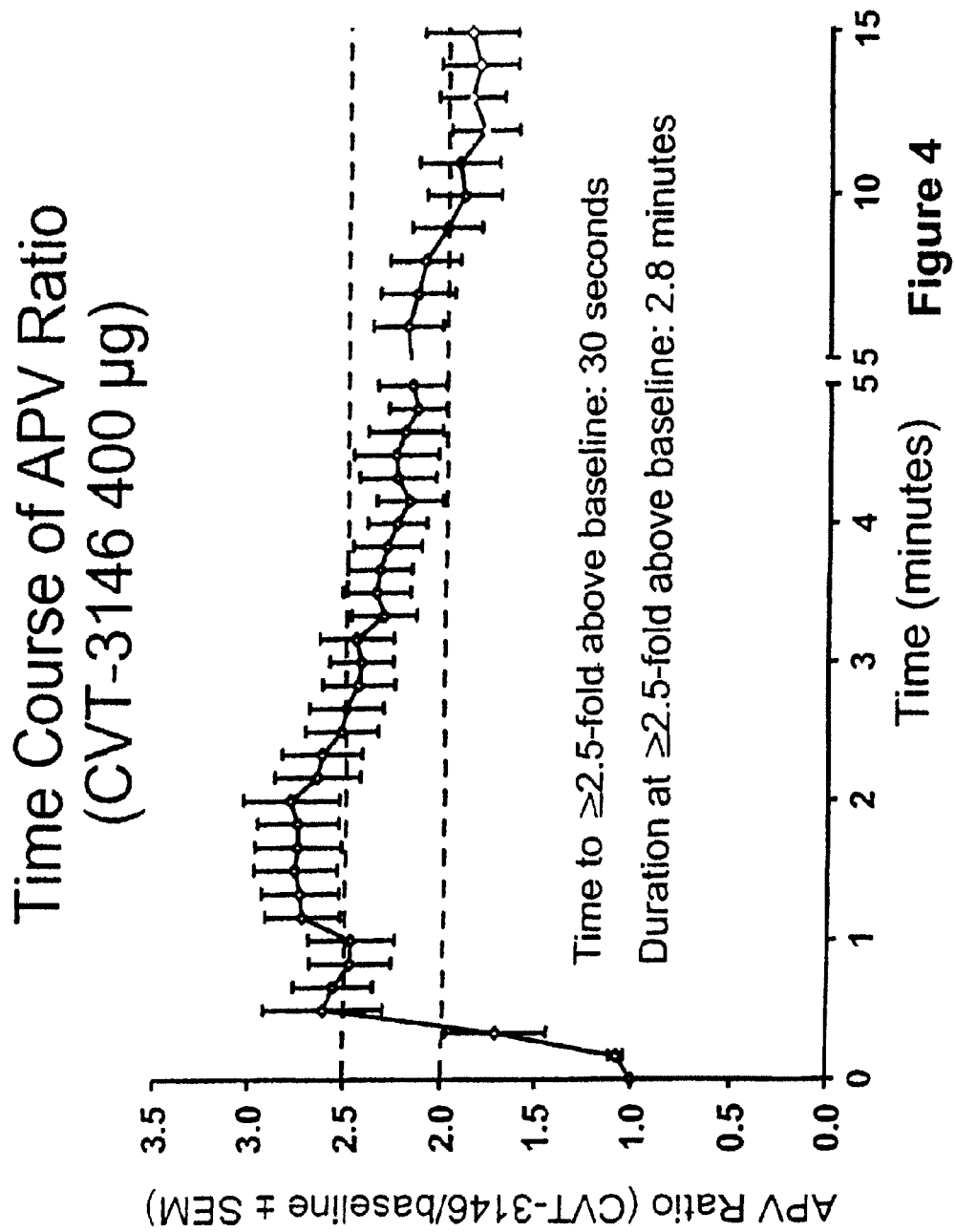
FIG. 4 is a plot of the time course of the average peak velocity (APV) ratio for human patients receiving 400 μg of CVT-3146 IV bolus.
Figure 5:
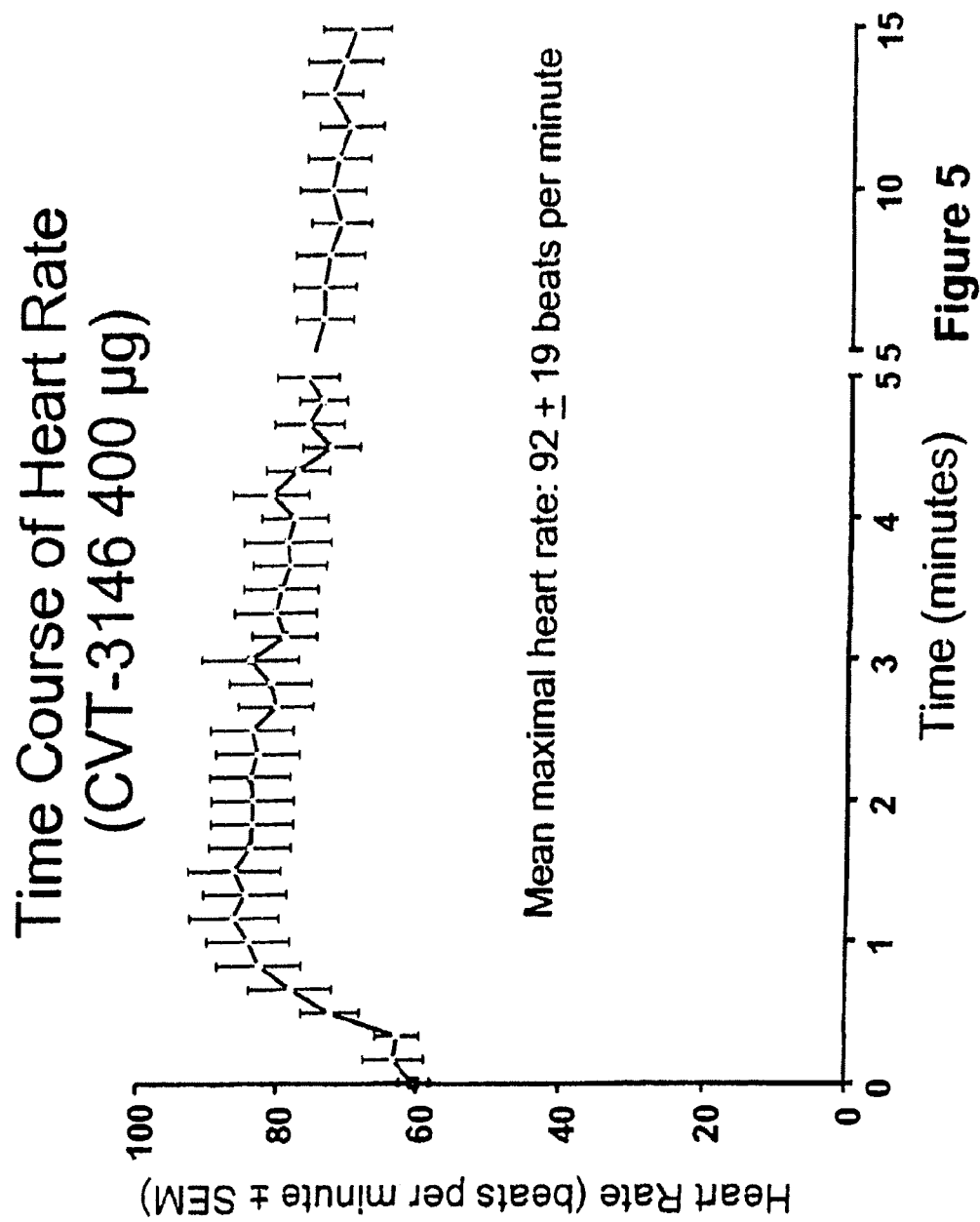
FIG. 5 is a plot of the time course of heart rate for human patients receiving 400 μg of CVT-3146 IV bolus.
Figure 6:
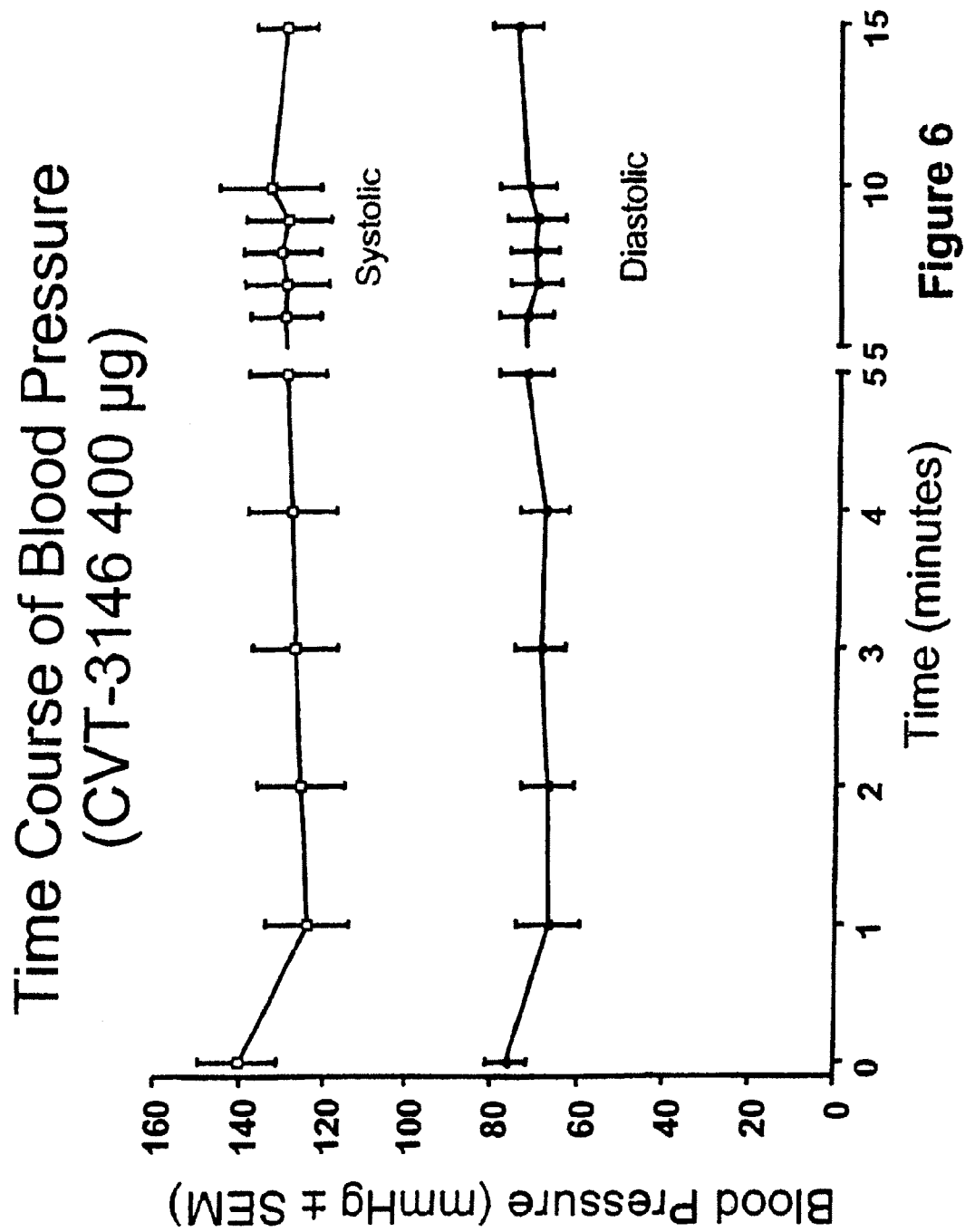
FIG. 6 is the time course of blood pressure for human patients receiving 400 μg of CVT-3146 IV bolus.
Figure 8:
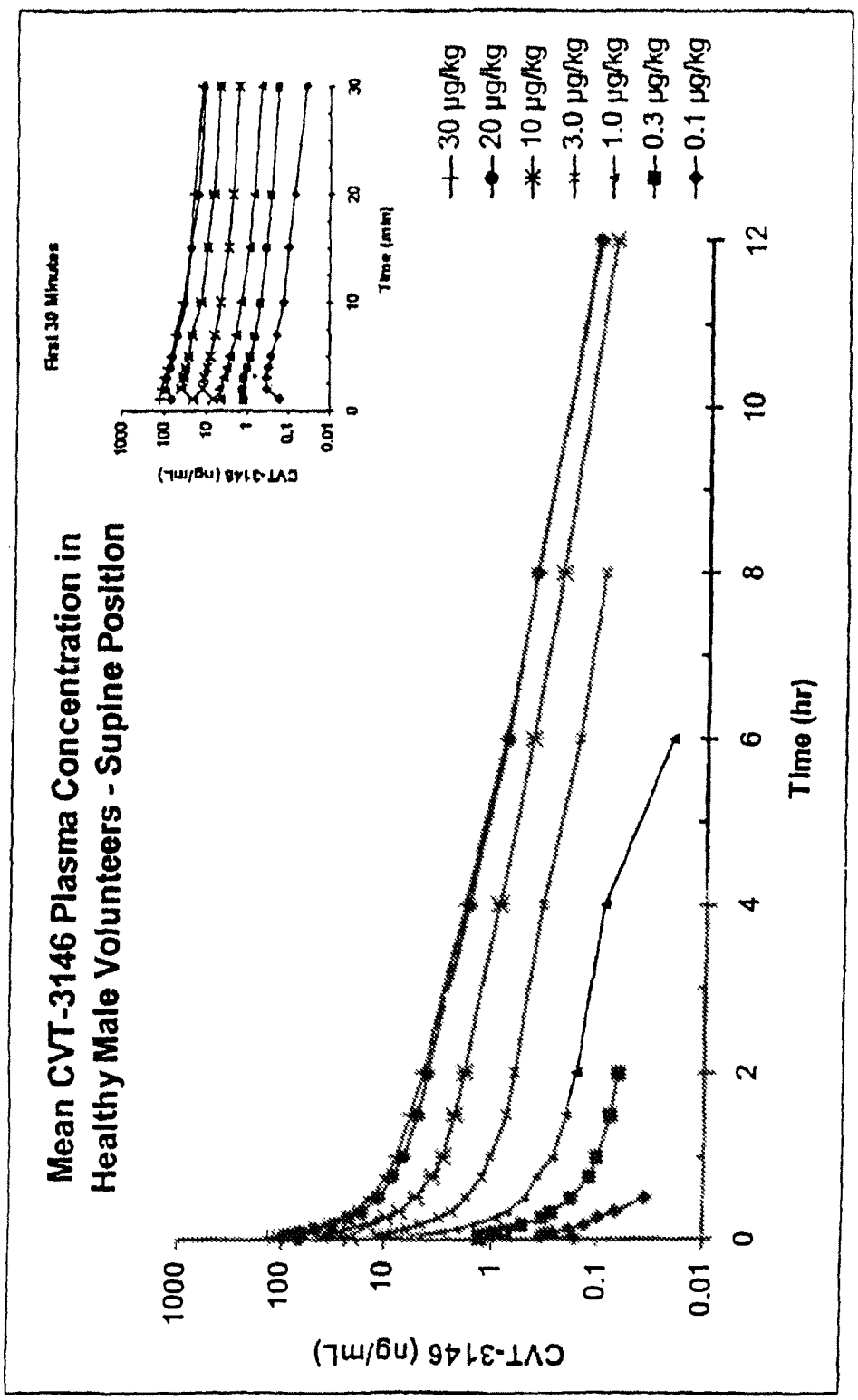
FIG. 8 is a plot of the change over time of mean CVT-3146 plasma concentration in healthy male volunteers in a supine position. The various curves relate to different amounts of CVT-3146 administered to the patients.
Figure 9:
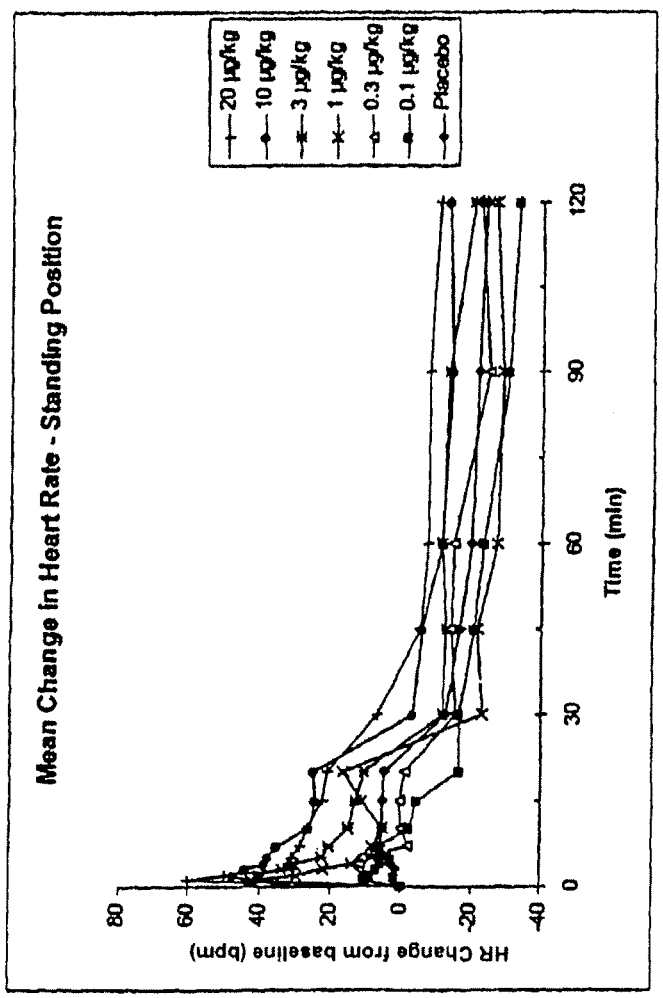
FIGS. 9 and 10 are plots of the mean change in heart rate of healthy male volunteers either in a standing position or in a supine position over time for various bolus dosing levels of CVT-3146.
Figure 10:
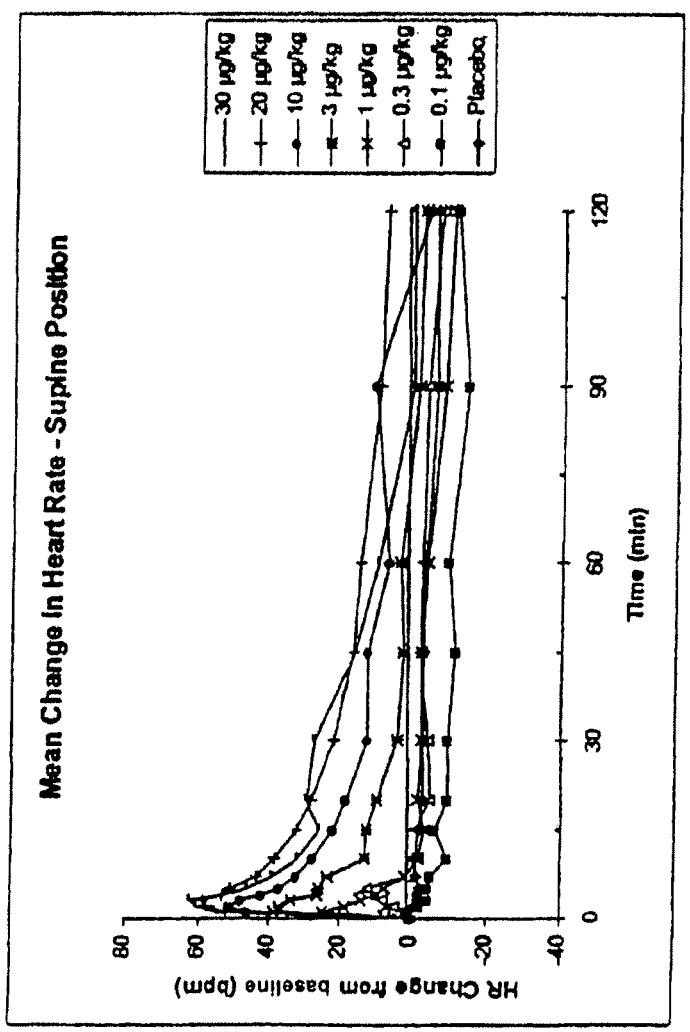
Figure 11:
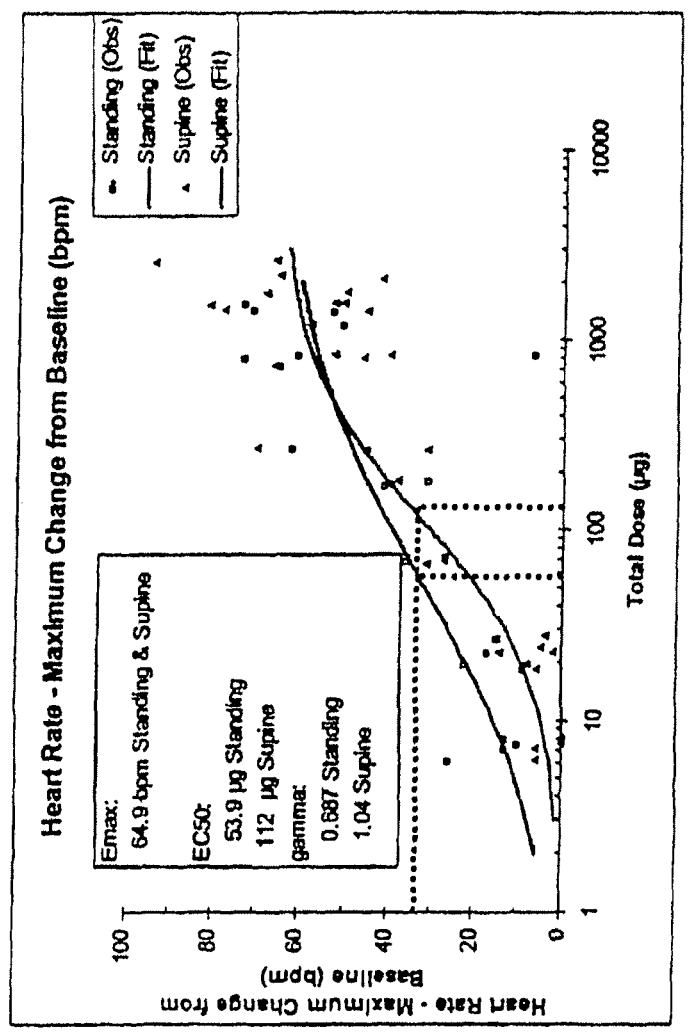
FIG. 11 is a plot of the maximum change in heart rate in relationship to the total dose of CVT-3146 administered to standing or supine human male patients. In the plot, the term "DBS" refers to the observed data point while "fit" refers to a curve fitted to the observed data points.
Figure 12:
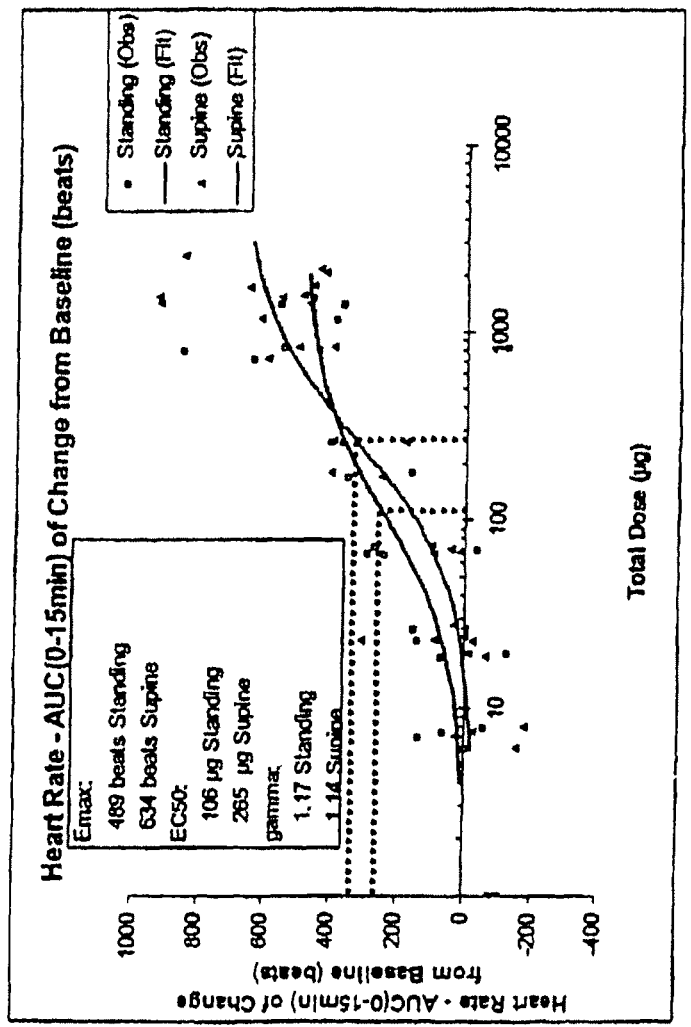
FIG. 12 is a plot of heart rate—(area under curve) AUC (0-15 min) of change from baseline in relationship to the total dose of CVT-3146 administered to standing or supine human subjects.
Figure 13:
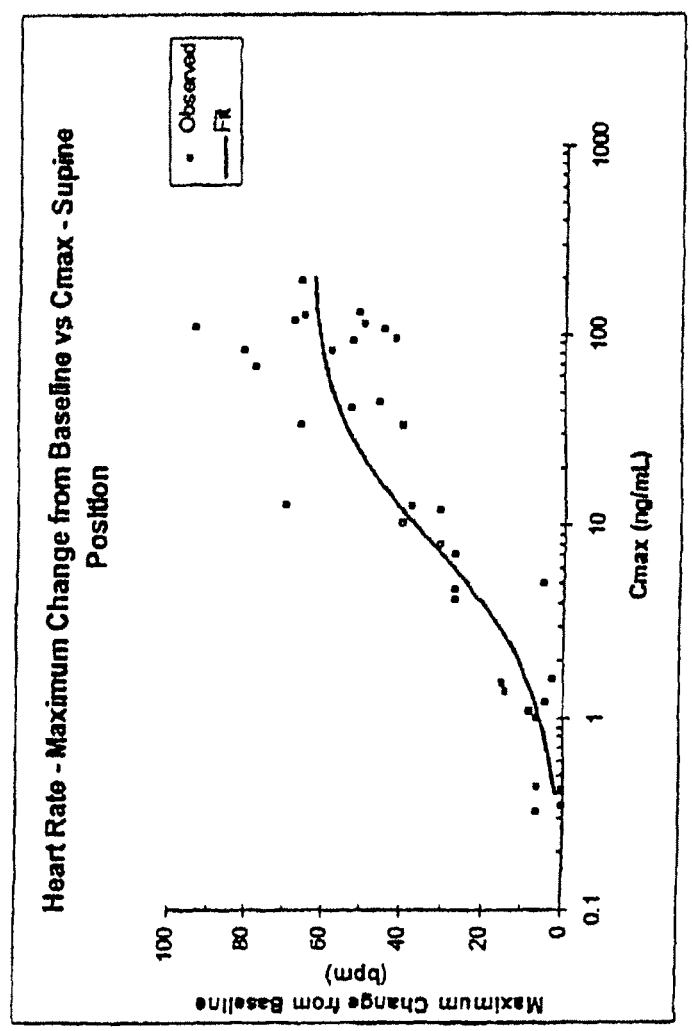
FIG. 13 is a plot of the maximum change from baseline heart rate at maximum plasma concentration of CVT-3146 for patients in a supine position.
Figure 14:
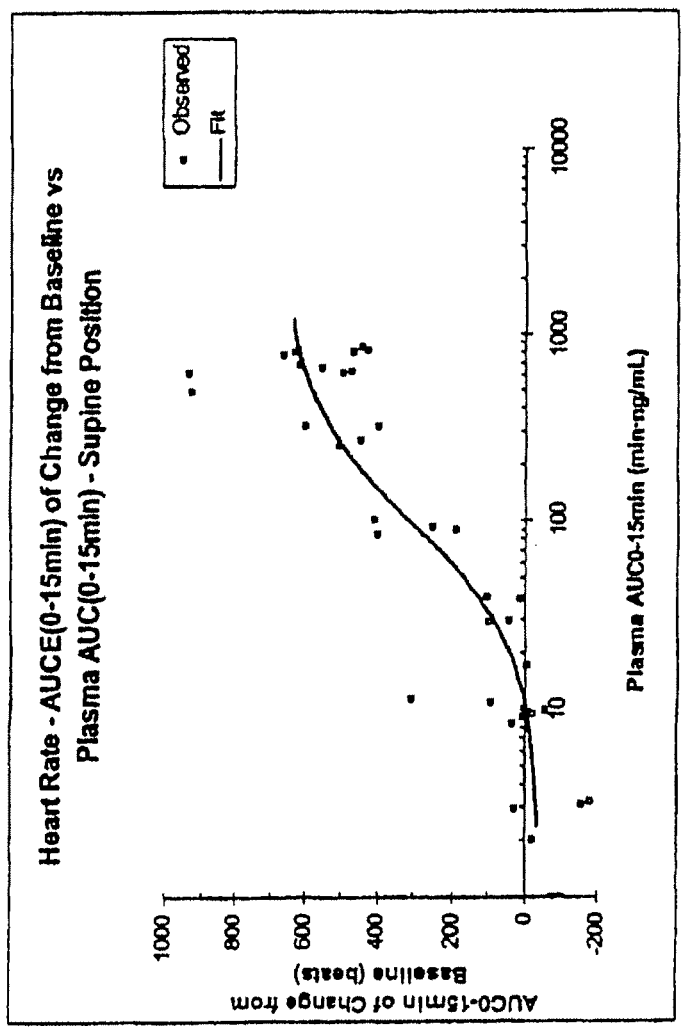
FIG. 14 is a plot of heart rate—(area under the curve-time v. effect) AUCE (0-15 min) of change from baseline versus plasma AUC (0-15 min) for patients in a supine position.
Figure 15:
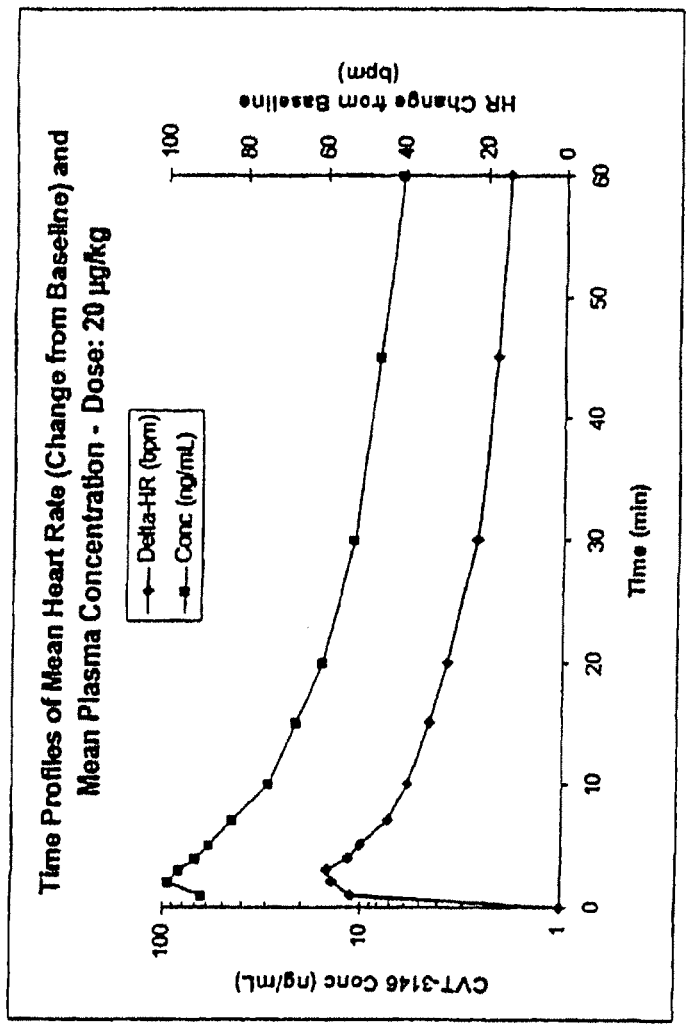
FIG. 15 is a plot of the time profiles of mean heart rate change from a baseline versus mean plasma concentration over time for a 20 μg/kg dose of CVT-3146.

Potent $A_{2A}$ agonists are useful as adjuncts in cardiac imaging when added either prior to dosing with an imaging agent or simultaneously with an imaging agent. Suitable imaging agents include $^{201}$Thallium or $^{99m}$Technetium-Sestamibi, $^{99mmTc}$teboroxime, and $^{99mmTc}$(III).

New and potent $A_{2A}$ agonists that increase CBF but do not significantly increase peripheral blood flow have been identified. The $A_{2A}$ agonists, and especially CVT-3146 and CVT-3033 have a rapid onset and a short duration when administered. An unexpected and newly identified benefit of these new compounds is that they are very useful when administered in a very small quantity in a single bolus intravenous (i.v.) injection. The $A_{2A}$ receptor agonists can be administered in amounts as little as 10 μg and as high as 600 μg or more and still be effective with few if any side-effects. An optimal dose may include as little as 10 μg and as much as about 1000 μg or more of a $A_{2A}$ receptor agonist. More preferably, an optimal dose will range from about 100 to about 500 μg of at least one $A_{2A}$ receptor agonist. It is preferred that the $A_{2A}$ receptor agonist is administered in a single bolus injection in an amount selected from about 300 μg, about 400 μg, about 500 μg, about 600 μg, and about 700 μg. These amounts are unexpectedly small when compared with adenosine which is typically administered continuously by IV infusion at a rate of about 140 μg/kg/min. Unlike adenosine, the same dosage of $A_{2A}$ receptor agonists, and in particular, CVT-3146 and CVT-3033 can be administered to a human patient regardless of the patient's weight. Thus, the administration of a single uniform amount of a $A_{2A}$ receptor agonists by iv bolus for myocardial imaging is dramatically simpler and less error prone than the time and weight dependent administration of adenosine. The dose of $A_{2A}$ receptor agonist administered to a human patient can, however, be determined by weight. Typically, a weight based dose will range from about 0.05 to about 60 μg/kg and more preferably from about 0.1 to about 30 CVT-3146 in particular is generally well tolerated when administered in an amount up to 10 μg/kg in standing patients and up to 20 μg/kg in supine patients.

$A_{2A}$ agonists of this invention may be administered orally, intravenously, through the epidermis or by any other means known in the art for administering therapeutic agents with bolus i.v. administration being preferred. In one embodiment, the bolus dosing occurs in 60 seconds or less. In yet other embodiments, the bolus dosing occurs in about 30 seconds or less, and more preferably in about 20 seconds or less or in about 10 seconds or less.

The $A_{2A}$ agonists of this invention are preferably administered in a single dose. The term "single dose" refers generally to a single quickly administered dose of a therapeutic amount of at least one $A_{2A}$ receptor agonist. The term "single dose" does not encompass a dose or doses administered over an extended period of time by, for example continuous i.v. infusion.

One aspect of this invention is directed to pharmaceutical compositions. The term "pharmaceutical composition" refers to the combination of one or more $A_{2A}$ agonist compounds of this invention with at least one liquid carrier that together form a solution or a suspension. Lyophilized powders including compositions of this invention fall within the scope of "pharmaceutical compositions" so long as the powders are intended to be reconstituted by the addition of a suitable liquid carrier prior to use. Examples of suitable liquid carriers include, but are not limited to water, distilled water, de-ionized water, saline, buffer solutions, normal isotonic saline solution, dextrose in water, and combinations thereof. Such pharmaceutical compositions are generally suitable for injection.

The term "buffer solution" or "buffer" as used herein refers to a solution containing both a weak acid and its conjugate weak base. The buffer solutions are used in pharmaceutical compositions of this invention in order to resist pH changes. Non-limiting examples of useful buffer solutions are solutions that comprise sodium bicarbonate and sodium phosphate.

A$_{2A}$ receptor agonists of this invention are prepared and then administered, with or without intervening storage, as a pharmaceutical composition. Various properties considered when formulating pharmaceutical compositions of this invention include, but are not limited to product shelf life, A$_{2A}$ receptor agonist solubility, composition pH, vein irritation, hemolysis, storage conditions (e.g., whether the pharmaceutical composition will be stored at room temperature or some other temperature) and the ability to withstand sterilization procedures.

One method to achieve the desired pharmaceutical composition properties is to include a co-solvent in the pharmaceutical composition. The co-solvent can be selected from any liquid or compound in solution that imparts the desired properties to the pharmaceutical composition. Examples of useful co-solvents include, but are not limited to methylboronic acid, borate buffer, propylene glycol, or polyethylene glycol. The amount of co-solvent in the pharmaceutical composition will depend upon properties, such as solubility and stability of the chosen A$_{2A}$ receptor agonist.

A preferred A$_{2A}$ receptor agonist of this invention is CVT-3146. CVT-3146 has solubility in water of about 50 micrograms/mL. Therefore, CVT-3146 can be dissolved and administered in water so long as the desired weight amount of CVT-3146 can be administered in an acceptable volume. For example, a preferred dose of about 400 micrograms can be administered in 8 mL of water. If this volume is too great for administration purposes, or if the pharmaceutical composition will be stored at other than room temperature (RT), then additional ingredients can be added to the composition to increase the solubility of CVT-3146 in the composition and/or to provide the resulting pharmaceutical composition with other improved properties such as improved stability and storage properties. Pharmaceutical compositions of this invention that include CVT-3146 may include up to about 1 milligram/mL of CVT-3146. It is preferred that pharmaceutical compositions including CVT-3146 include from about 50 to about 250 micrograms/mL, and more preferably from about 50 to 150 micrograms/mL of CVT-3146.

In order to improve their solubility and storage properties, A$_{2A}$ receptor agonists of this invention can be administered in a pharmaceutical composition including a methylboronic acid (MBA) co-solvent. The methylboronic acid is added to the pharmaceutical composition to improve agonist solubility and shelf life. MBA increases the pH of the resulting composition. The solubility of CVT-3146 in a pharmaceutical composition including MBA tends to decrease as the composition pH drops towards neutral. Therefore, with CVT-3146, an optimal MBA-containing composition pH is from about 8.5 to 10 with a pH of about 9.1 to about 9.4 being preferred and a pH of about 9.3 being most preferred. This corresponds to a composition including from about 50 to about 250 mg/mL of MBA. As an alternative to MBA, CVT-3146 can be combined with a borate buffer solution. Typically, a borate buffer solution will be comprised of an aqueous solution of sodium borate that is adjusted to the desired pH such as a pH of 9.3 using an acid or a base.

MBA containing pharmaceutical compositions can suffer from storage problems. Namely, MBA can cause delamination when packaged in certain type I glass vessels. This problem can be overcome by storing the MBA containing pharmaceutical compositions in plastic vessels or in more resistant type I glass vessels.

If A$_{2A}$ receptor agonist containing pharmaceutical compositions having a pH closer to neutral are desired, then an alternative is to combine A$_{2A}$ receptor agonists with a propylene glycol (PG) co-solvent. The amount of PG used in the composition may range from about 5% to up to 25% by volume with a range of about 8% to about 20% by volume being more preferred when using CVT-3146. An alternative to PG is polyethylene glycol—PEG. A preferred PEG will have an average molecular weight of from about 200 to 400.

Preferably, the CVT-3146 composition including PG or PEG will have a pH of from about 6 to about 8 with a pH of about 7 being preferred. Any physiologically acceptable buffer capable of adjusting the composition pH to the desired value can be used. Additional optional ingredients such as EDTA and dimethylacetamide could be employed in the composition as well.

The pharmaceutical compositions of this invention may include one or more anti-oxidants such as butylated hydroxyanisole (BHA).

A first class of compounds that are potent and selective agonists for the A$_{2A}$ adenosine receptor that are useful in the methods of this invention are 2-adenosine N-pyrazole compounds having the formula:

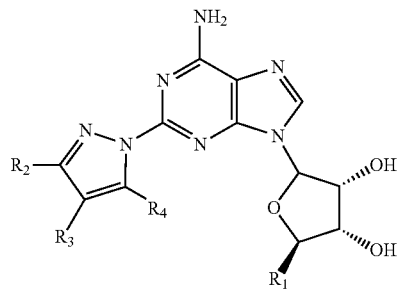

wherein R$^1$=CH$_2$OH or —C(=O)NR$^5$R$^6$;
R$^3$ is independently selected from the group consisting of C$_{1-15}$ alkyl, halo, NO$_2$, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$, —CONR$^7$R$^8$, C$_{2-15}$ alkenyl, C$_{2-15}$ alkynyl, heterocyclyl, aryl, and heteroaryl, wherein the alkyl, alkenyl, alkynyl, aryl, heterocyclyl and heteroaryl substituents are optionally substituted with from 1 to 3 substituents independently selected from the group consisting of halo, alkyl, NO$_2$, heterocyclyl, aryl, heteroaryl, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^2$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ and wherein the optional substituted heteroaryl, aryl, and heterocyclyl substituents are optionally substituted with halo, NO$_2$, alkyl, CF$_3$, amino, mono- or di-alkylamino, alkyl or aryl or heteroaryl amide, NCOR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, SR$^{20}$, S(O)R$^{22}$, SO$_2$R$^{22}$, SO$_2$N(R$^{20}$)$_2$, CN, or OR$^{20}$;

R$^5$ and R$^6$ are each individually selected from H, and C$_{1-15}$ alkyl that is optionally substituted with from 1 to 2 substituents independently selected from the group of halo, NO$_2$, heterocyclyl, aryl, heteroaryl, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, $SO_2NR^{20}CO_2R^{22}$, $SO_2NR^{20}CON(R^{20})_2$, $N(R^{20})_2$ $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ wherein each optional substituted heteroaryl, aryl, and heterocyclyl substituent is optionally substituted with halo, $NO_2$, alkyl, $CF_3$, amino, monoalkylamino, dialkylamino, alkylamide, arylamide, heteroarylamide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^7$ is selected from the group consisting of hydrogen, $C_{1-15}$ alkyl, $C_{2-15}$ alkenyl, $C_{2-15}$ alkynyl, heterocyclyl, aryl and heteroaryl, wherein the alkyl, alkenyl, alkynyl, aryl, heterocyclyl and heteroaryl substituents are optionally substituted with from 1 to 3 substituents independently selected from the group of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$ and $OCON(R^{20})_2$ and wherein each optional substituted heteroaryl, aryl and heterocyclyl substituent is optionally substituted with halo, $NO_2$, alkyl, $CF_3$, amino, mono- or dialkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^8$ is selected from the group consisting of hydrogen, $C_{1-15}$ alkyl, $C_{2-15}$ alkenyl, $C_{2-15}$ alkynyl, heterocyclyl, aryl, and heteroaryl, wherein the alkyl, alkenyl, alkynyl, aryl, heterocyclyl, and heteroaryl substituents are optionally substituted with from 1 to 3 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional substituted heteroaryl, aryl, and heterocyclyl substituent is optionally substituted with halo, $NO_2$, alkyl, $CF_3$, amino, mono- or dialkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl;

$R^{22}$ is selected from the group consisting of $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and wherein $R^2$ and $R^4$ are selected from the group consisting of H, $C_{1-6}$ alkyl and aryl, wherein the alkyl and aryl substituents are optionally substituted with halo, CN, $CF_3$, $OR^{20}$ and $N(R^{20})_2$ with the proviso that when $R^2$ is not hydrogen then $R^4$ is hydrogen, and when $R^4$ is not hydrogen then $R^2$ is hydrogen.

In a related group of compounds of this invention, $R^3$ is selected from the group consisting of $C_{1-15}$ alkyl, halo, $CF_3$, CN, $OR^{20}$, $SR^{20}$, $S(O)R^{22}$, $SO_2R^{22}$, $SO_2N(R^{20})_2$, $COR^{22}$, $CO_2R^{20}$, —$CONR^7R^8$, aryl and heteroaryl wherein the alkyl, aryl and heteroaryl substituents are optionally substituted with from 1 to 3 substituents independently selected from the group consisting of halo, aryl, heteroaryl, $CF_3$, CN, $OR^{20}$, $SR^{20}$, $S(O)R^{22}$, $SO_2R^{22}$, $SO_2N(R^{20})_2$, $COR^{20}$, $CO_2R^{20}$ or $CON(R^{20})_2$, and each optional heteroaryl and aryl substituent is optionally substituted with halo, alkyl, $CF_3$, CN, and $OR^{20}$; $R^5$ and $R^6$ are independently selected from the group of H and $C_1$-$C_{15}$ alkyl including one optional aryl substituent and each optional aryl substituent that is optionally substituted with halo or $CF_3$; $R^7$ is selected from the group consisting of $C_{1-15}$ alkyl, $C_{2-15}$ alkynyl, aryl, and heteroaryl, wherein the alkyl, alkynyl, aryl, and heteroaryl substituents are optionally substituted with from 1 to 3 substituents independently selected from the group consisting of halo, aryl, heteroaryl, $CF_3$, CN, $OR^{20}$, and each optional heteroaryl and aryl substituent is optionally substituted with halo, alkyl, $CF_3$, CN, or $OR^{20}$; $R^8$ is selected from the group consisting of hydrogen and $C_{1-15}$ alkyl; $R^{20}$ is selected from the group consisting of H, $C_{1-4}$ alkyl and aryl, wherein alkyl and aryl substituents are optionally substituted with one alkyl substituent; and $R^{22}$ is selected from the group consisting of $C_{1-4}$ alkyl and aryl which are each optionally substituted with from 1 to 3 alkyl groups.

In yet another related class of compounds, $R^1$ is $CH_2OH$; $R^3$ is selected from the group consisting of $CO_2R^{20}$, —$CONR^7R^8$ and aryl where the aryl substituent is optionally substituted with from 1 to 2 substituents independently selected from the group consisting of halo, $C_{1-6}$ alkyl, $CF_3$ and $OR^{20}$; $R^7$ is selected from the group consisting of hydrogen, $C_{1-8}$ alkyl and aryl, where the alkyl and aryl substituents are optionally substituted with one substituent selected from the group consisting of halo, aryl, $CF_3$, CN, $OR^{20}$ and wherein each optional aryl substituent is optionally substituted with halo, alkyl, $CF_3$, CN, and $OR^{20}$; $R^8$ is selected from the group consisting of hydrogen and $C_{1-8}$ alkyl; and $R^{20}$ is selected from hydrogen and $C_{1-4}$ alkyl.

In a still another related class of compounds of this invention, $R^1$=$CH_2OH$; $R^3$ is selected from the group consisting of $CO_2R^{20}$, —$CONR^7R^8$, and aryl that is optionally substituted with one substituent selected from the group consisting of halo, $C_{1-3}$ alkyl and $OR^{20}$; $R^7$ is selected from hydrogen, and $C_{1-3}$ alkyl; $R^8$ is hydrogen; and $R^{20}$ is selected from hydrogen and $C_{1-4}$ alkyl. In this preferred embodiment, $R^3$ is most preferably selected from —$CO_2Et$ and —$CONHEt$.

In yet another related class of compounds, $R^1$=—$CONHEt$, $R^3$ is selected from the group consisting of $CO_2R^{20}$, —$CONR^7R^8$, and aryl in that aryl is optionally substituted with from 1 to 2 substituents independently selected from the group consisting of halo, $C_{1-3}$ alkyl, $CF_3$ or $OR^{20}$; $R^7$ is selected from the group consisting of hydrogen, and $C_{1-8}$ alkyl that is optionally substituted with one substituent selected from the group consisting of halo, $CF_3$, CN or $OR^{20}$; $R^8$ is selected from the group consisting of hydrogen and $C_{1-3}$ alkyl; and $R^{20}$ is selected from the group consisting of hydrogen and $C_{1-4}$ alkyl. In this more preferred embodiment, $R^8$ is preferably hydrogen, $R^7$ is preferably selected from the group consisting of hydrogen, and $C_{1-3}$ alkyl, and $R^{20}$ is preferably selected from the group consisting of hydrogen and $C_{1-4}$ alkyl.

Specific useful compounds are selected from ethyl 1-{9-[(4S,2R,3R,5R)-3,4-dihydroxy-5-(hydroxymethyl)oxolan-2-yl]-6-aminopurin-2-yl}pyrazole-4-carboxylate, (4S,2R,3R,5R)-2-{6-amino-2-[4-(4-chlorophenyl)pyrazolyl]purin-9-yl}-5-(hydroxymethyl)oxolane-3,4-diol, (4S,2R,3R,5R)-2-{6-amino-2-[4-(4-methoxyphenyl)pyrazolyl]purin-9-yl}-5-(hydroxymethyl)oxolane-3,4-diol, (4S,2R,3R,5R)-2-{6-amino-2-[4-(4-methylphenyl)pyrazolyl]purin-9-yl}-5-(hydroxymethyl)oxolane-3,4-diol, (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide, 1-{9-[(4S,2R,3R,5R)-3,4-dihydroxy-5-(hydroxymethyl)oxolan-2-yl]-6-aminopurin-2-yl}pyrazole-4-carboxylic acid, (1-{9-[(4S,2R,3R,5R)-3,4-dihydroxy-5-(hydroxymethyl)oxolan-2-yl]-6-aminopurin-2-yl}pyrazol-4-yl)-N,N-dimethylcarboxamide, (1-{9-[(4S,2R,3R,5R)-3,4-dihydroxy-5-(hydroxymethyl)oxolan-2-yl]-6-aminopurin-2-yl}pyrazol-4-yl)-N-ethylcarboxamide, 1-{9-[(4S,2R,3R,5R)-3,4-dihydroxy-5-(hydroxymethyl)oxolan-2-yl]-6-aminopurin-2-yl}pyrazole-4-carboxamide, 1-{9-[(4S,2R,3R,5R)-3,4-dihydroxy-5-(hydroxymethyl)oxolan-2-yl]-6-aminopurin-2-yl}pyrazol-4-yl)-N-(cyclopentylmethyl)carboxamide, (1-{9-[(4S,2R,3R,5R)-3,4-dihydroxy-5-(hydroxymethyl)oxolan-2-yl]-6-aminopurin-2-yl}pyrazol-4-yl)-N-[(4-chlorophenyl)methyl]carboxamide, Ethyl 2-[(1-{9-[(4S,2R,3R,5R)-3,4-dihydroxy-5-(hydroxymethyl)oxolan-2-yl]-6-aminopurin-2-yl}pyrazol-4-yl)carbonylamino]acetate, and mixtures thereof.

A second class of compounds that are potent and selective agonists for the $A_{2A}$ adenosine receptor that are useful in the methods of this invention are 2-adenosine C-pyrazole compounds having the following formula:

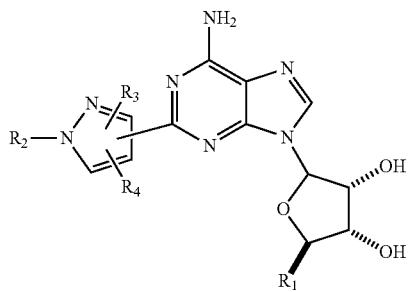

wherein $R^1$ is —$CH_2OH$ or —$C(=O)NR^5R^6$;

$R^2$ is selected from the group consisting of hydrogen, $C_{1-15}$ alkyl, $C_{2-15}$ alkenyl, $C_{2-15}$ alkynyl, heterocyclyl, aryl, and heteroaryl, wherein the alkyl, alkenyl, alkynyl, aryl, heterocyclyl, and heteroaryl substituents are optionally substituted with from 1 to 3 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heteroaryl, aryl, and heterocyclyl substituent is optionally substituted with halo, $NO_2$, alkyl, $CF_3$, amino, mono- or di-alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^3$ and $R^4$ are individually selected from the group consisting of hydrogen, $C_{1-15}$ alkyl, $C_{2-15}$ alkenyl, $C_{2-15}$ alkynyl, heterocyclyl, aryl, and heteroaryl, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ wherein the alkyl, alkenyl, alkynyl, aryl, heterocyclyl, and heteroaryl substituents are optionally substituted with from 1 to 3 substituents individually selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heteroaryl, aryl, and heterocyclyl substituent is optionally substituted with halo, $NO_2$, alkyl, $CF_3$, amino, mono- or di-alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^5$ and $R^6$ are each individually H, $C_{1-15}$ alkyl with from 1 to 2 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heteroaryl, aryl, and heterocyclyl substituent is optionally substituted with halo, $NO_2$, alkyl, $CF_3$, amino, mono- or di-alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and $R^{22}$ is a member selected from the group consisting of $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, and heteroaryl wherein, when $R^1=CH_2OH$, $R^3$ is H, $R^4$ is H, the pyrazole ring is attached through $C^4$, and $R^2$ is not H.

When the compound is selected has one of the following formulas:

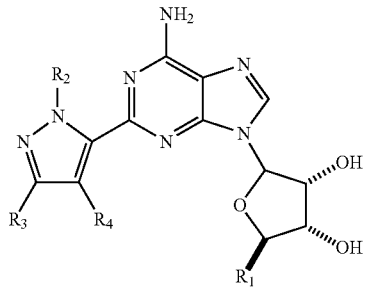

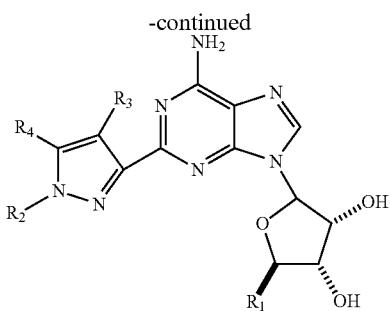

then it is preferred that R¹ is —CH₂OH; R² is selected from the group consisting of hydrogen, $C_{1-8}$ alkyl wherein the alkyl is optionally substituted with one substituent independently selected from the group consisting of aryl, $CF_3$, CN, and wherein each optional aryl substituent is optionally substituted with halo, alkyl, $CF_3$ or CN; and R³ and R⁴ are each independently selected from the group consisting of hydrogen, methyl and more preferably, R³ and R⁴ are each hydrogen.

When the compound of this invention has the following formula:

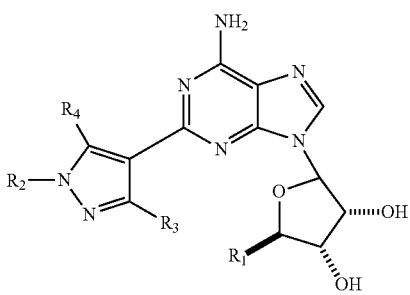

then it is preferred that R¹ is —CH₂OH; R² is selected from the group consisting of hydrogen, and $C_{1-6}$ alkyl optionally substituted by phenyl. More preferably, R² is selected from benzyl and pentyl; R³ is selected from the group consisting of hydrogen, $C_{1-6}$ alkyl, aryl, wherein the alkyl, and aryl substituents are optionally substituted with from 1 to 2 substituents independently selected from the group consisting of halo, aryl, $CF_3$, CN, and wherein each optional aryl substituent is optionally substituted with halo, alkyl, $CF_3$ or CN; and R⁴ is selected from the group consisting of hydrogen and $C_{1-6}$ alkyl, and more preferably, R⁴ is selected from hydrogen and methyl.

A more specific class of compounds is selected from the group consisting of (4S,2R,3R,5R)-2-{6-amino-2-[1-benzylpyrazol-4-yl]purin-9-yl}-5-(hydroxymethyl)oxolane-3,4-diol, (4S,2R,3R,5R)-2-[6-amino-2-(1-pentylpyrazol-4-yl)purin-9-yl]-5-(hydroxymethyl)oxolane-3,4-diol, (4S,2R,3R,5R)-2-[6-amino-2-(1-methylpyrazol-4-yl)purin-9-yl]-5-(hydroxymethyl)oxolane-3,4-diol, (4S,2R,3R,5R)-2-{6-amino-2-[1-(methylethyl)pyrazol-4-yl]purin-9-yl}-5-(hydroxymethyl)oxolane-3,4-diol, (4S,2R,3R,5R)-2-{6-amino-2-[1-(3-phenylpropyl)pyrazol-4-yl]purin-9-yl}-5-(hydroxymethyl)oxolane-3,4-diol, (4S,2R,3R,5R)-2-{6-amino-2-[1-(4-t-butylbenzyl)pyrazol-4-yl]purin-9-yl}-5-(hydroxymethyl)oxolane-3,4-diol, (4S,2R,3R,5R)-2-(6-amino-2-pyrazol-4-ylpurin-9-yl)-5-(hydroxymethyl)oxolane-3,4-diol, (4S,2R,3R,5R)-2-{6-amino-2-[1-pent-4-enylpyrazol-4-yl]purin-9-yl}-5-(hydroxymethyl)oxolane-3,4-diol, (4S,2R,3R,5R)-2-{6-amino-2-[1-decylpyrazol-4-yl]purin-9-yl}-5-(hydroxymethyl)oxolane-3,4-diol, (4S,2R,3R,5R)-2-{6-amino-2-[1-(cyclohexylmethyl)pyrazol-4-yl]purin-9-yl}-5-(hydroxymethyl)oxolane-3,4-diol, (4S,2R,3R,5R)-2-{6-amino-2-[1-(2-phenylethyl)pyrazol-4-yl]purin-9-yl}-5-(hydroxymethyl)oxolane-3,4-diol, (4S,2R,3R,5R)-2-{6-amino-2-[1-(3-cyclohexylpropyl)pyrazol-4-yl]purin-9-yl}-5-(hydroxymethyl)oxolane-3,4-diol, (4S,2R,3R,5R)-2-{6-amino-2-[1-(2-cyclohexylethyl)pyrazol-4-yl]purin-9-yl}-5-(hydroxymethyl)oxolane-3,4-diol, and combinations thereof.

A very useful and potent and selective agonists for the $A_{2A}$ adenosine receptor is CVT-3146 or (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide which has the formula:

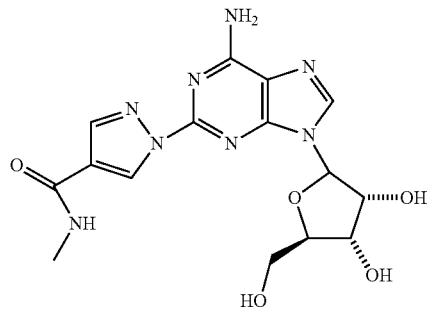 [SMILES: CNC(=O)c1cnn(-c2nc(N)c3ncn(C4O[C@H](CO)[C@@H](O)[C@H]4O)c3n2)c1]

Another preferred compound that is useful as a selective $A_{2A}$-adenosine receptor agonist with a short duration of action is a compound of the formula:

CVT-3033

CVT-3033 is particularly useful as an adjuvant in cardiological imaging.

The first and second classes of compounds identified above are described in more detail in U.S. Pat. Nos. 6,403,567 and 6,214,807, the specification of each of which is incorporated herein by reference.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1-15, more preferably 1 to 8, even more preferably 1-6, yet more preferably 1-4 and most preferably 1-2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3-8, more preferably 3-6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2-20, preferably 2-17, more preferably 2-10, even more preferably 2-8, most preferably 2-4, carbon atoms and at least one, preferably 1-3, more preferably 1-2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2-20, preferably 2-17, more preferably 2-10, even more preferably 2-8, most preferably 2-4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'''R'''', where R is lower alkyl, or substituted lower alkyl, R', R''', R'''' may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl, substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently be hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5-7, more preferably 5-6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo [b]thienyl) and having at least one heteroatom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen atom to produce a stable compound.

"Heterocyclyl"—alone or in combination means a non-aromatic cycloalkyl group having from 5 to 10 atoms in which from 1 to 3 carbon atoms in the ring are replaced by heteroatoms of 0, S or N, and are optionally benzo fused or fused heteroaryl of 5-6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted heterocyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The first class of compounds identified above can be prepared as outlined in Schemes 1-4.

Compounds having the general formula IV can be prepared as shown in Scheme 1.

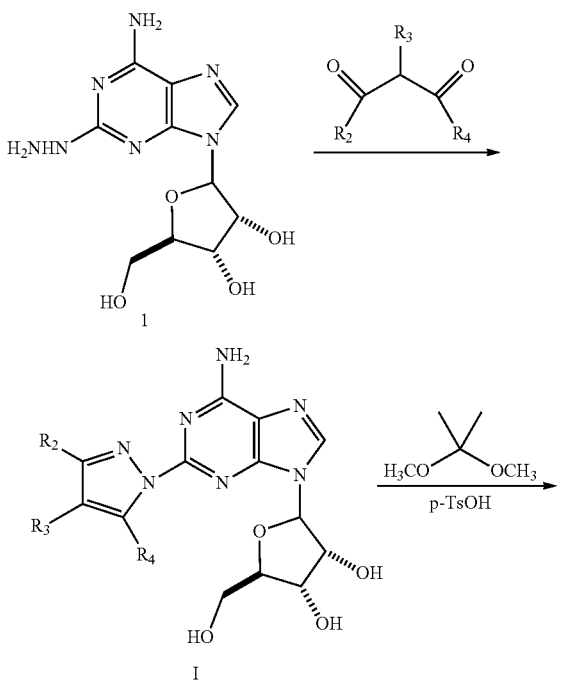

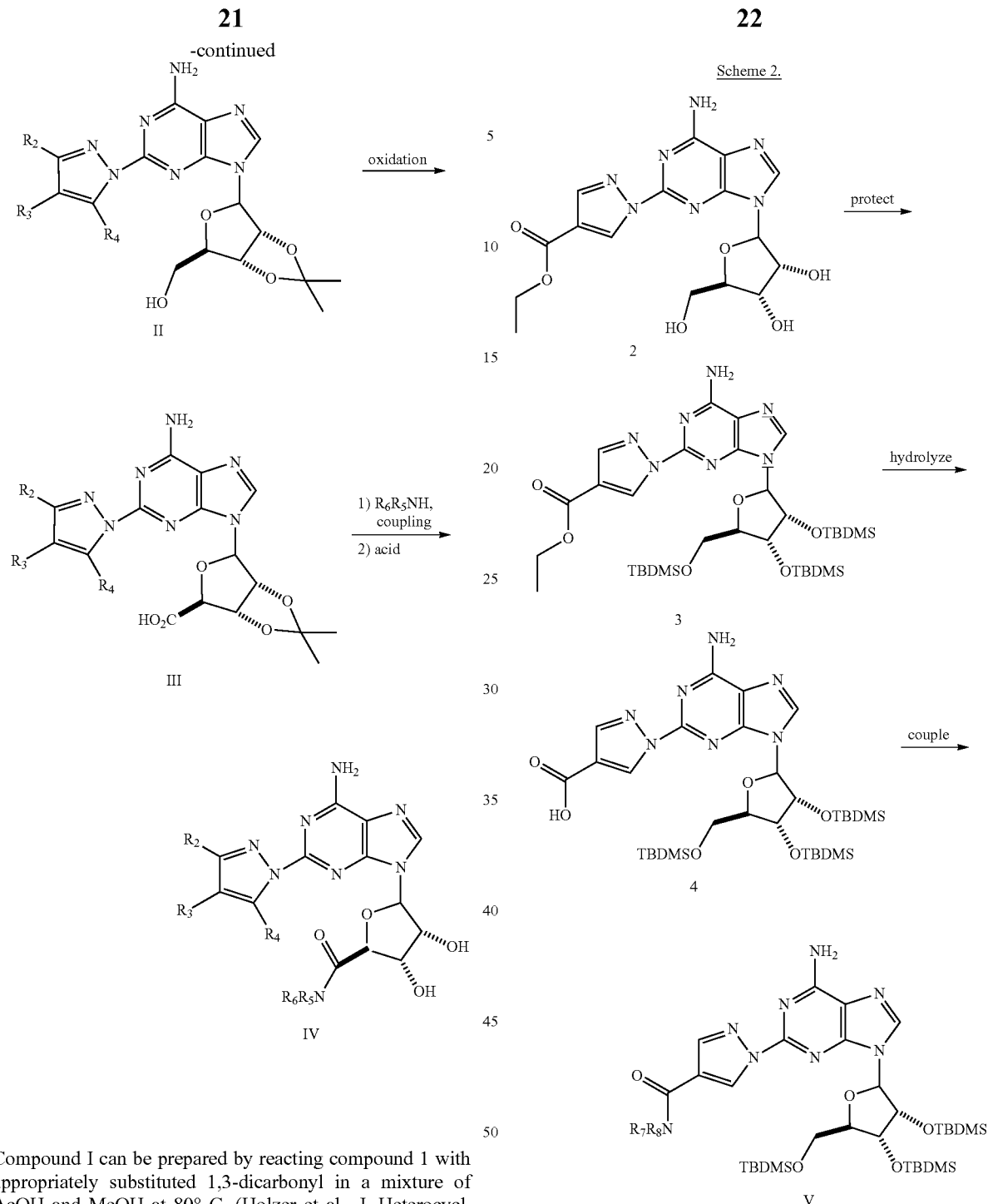

Compound I can be prepared by reacting compound 1 with appropriately substituted 1,3-dicarbonyl in a mixture of AcOH and MeOH at 80° C. (Holzer et al., J. Heterocycl. Chem. (1993) 30, 865). Compound II, which can be obtained by reacting compound I with 2,2-dimethoxypropane in the presence of an acid, can be oxidized to the carboxylic acid III, based on structurally similar compounds using potassium permanganate or pyridinium chlorochromate (M. Hudlicky, (1990) Oxidations in Organic Chemistry, ACS Monographs, American Chemical Society, Washington D.C.). Reaction of a primary or secondary amine having the formula $R_6R_5NH$, and compound III using DCC (M. Fujino et al., Chem. Pharm. Bull. (1974), 22, 1857), PyBOP (J. Martinez et al., J. Med. Chem. (1988) 28, 1874) or PyBrop (J. Caste et al. Tetrahedron, (1991), 32, 1967) coupling conditions can afford compound IV.

Compound V can be prepared as shown in Scheme 2. The Tri TBDMS derivative 4 can be obtained by treating compound 2 with TBDMSCl and imidazole in DMF followed by hydrolysis of the ethyl ester using NaOH. Reaction of a primary or secondary amine with the formula $R_7R_8NH$, and compound 4 using DCC (M. Fujino et al., Chem. Pharm. Bull. (1974), 22, 1857), PyBOP (J. Martinez et al., J. Med. Chem. (1988) 28, 1874) or PyBrop (J. Caste et al. Tetrahedron, (1991), 32, 1967) coupling conditions can afford compound V.

Scheme 3.

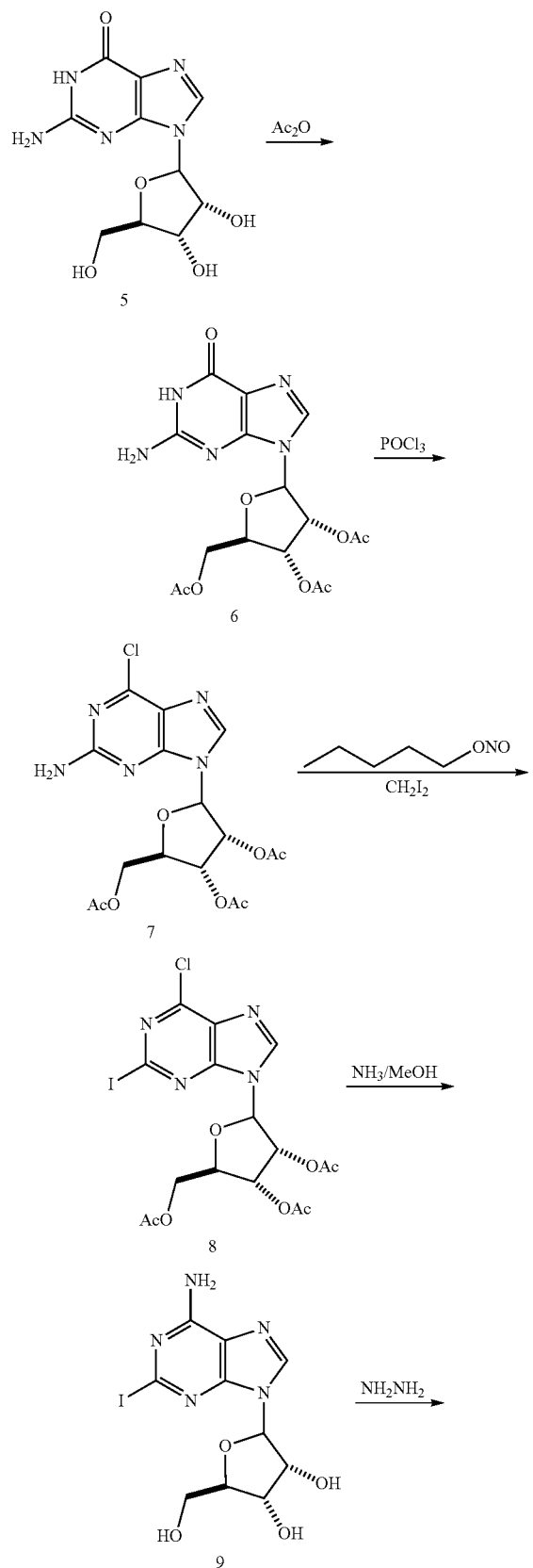

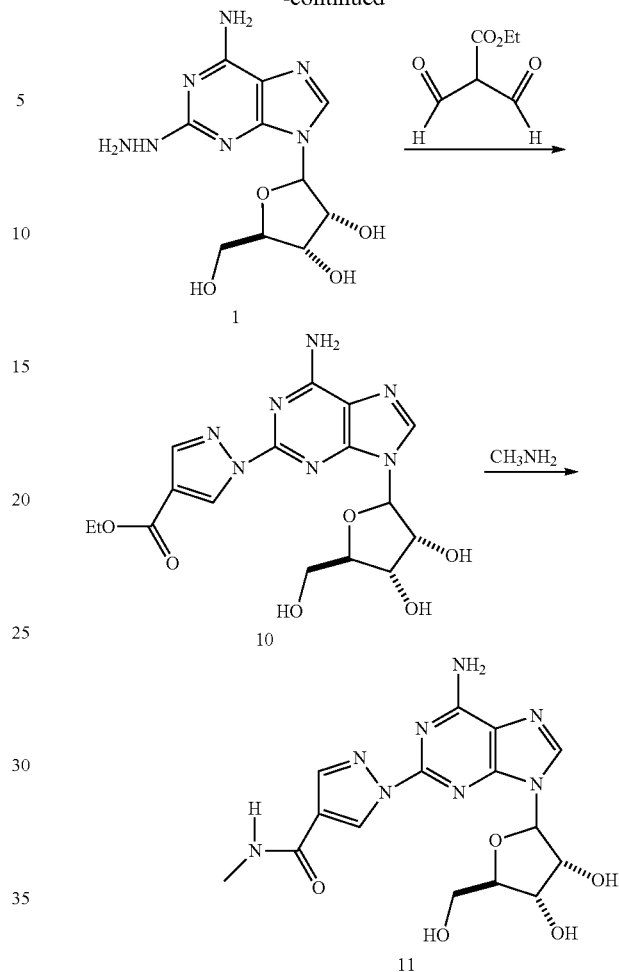

A specific synthesis of Compound 11 is illustrated in Scheme 3. Commercially available guanosine 5 was converted to the triacetate 6 as previously described (M. J. Robins and B. Uznanski, Can. J. Chem. (1981), 59, 2601-2607). Compound 7, prepared by following the literature procedure of Gerster et al. (J. F. Gerster, A. F. Lewis, and R. K. Robins, In Synthetic procedures in nucleic acid chemistry. Vol. 1. Edited by W. W. Zorbach and R. S. Tipson. Wiley-Interscience, New York. 1968. pp. 242-243), was converted to compound 9 in two steps as previously described (V. Nair et al., J. Org. Chem., (1988), 53, 3051-3057). Compound 1 was obtained by reacting hydrazine hydrate with compound 9 in ethanol at 80° C. Condensation of compound 1 with ethoxycarbonylmalondialdehyde in a mixture of AcOH and MeOH at 80° C. produced compound 10. Heating compound 10 in excess methylamine afforded compound 11.

Scheme 4

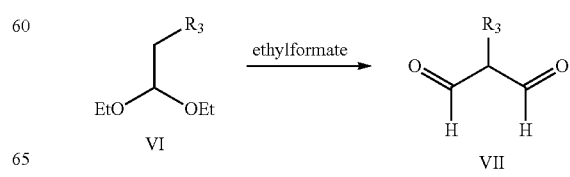

The synthesis of 1,3-dialdehyde VII is described in Scheme 4. Reaction of 3,3-diethoxypropionate or 3,3-diethoxypropionitrile or 1,1-diethoxy-2-nitroethane VI ($R_3$=$CO_2R$, CN or $NO_2$) with ethyl or methyl formate in the presence of NaH can afford the dialdehyde VII (Y. Yamamoto et al., J. Org. Chem. (1989) 54, 4734).

The second class of compounds described above may be prepared by as outlined in schemes 1-5. Compounds having the general formula II:

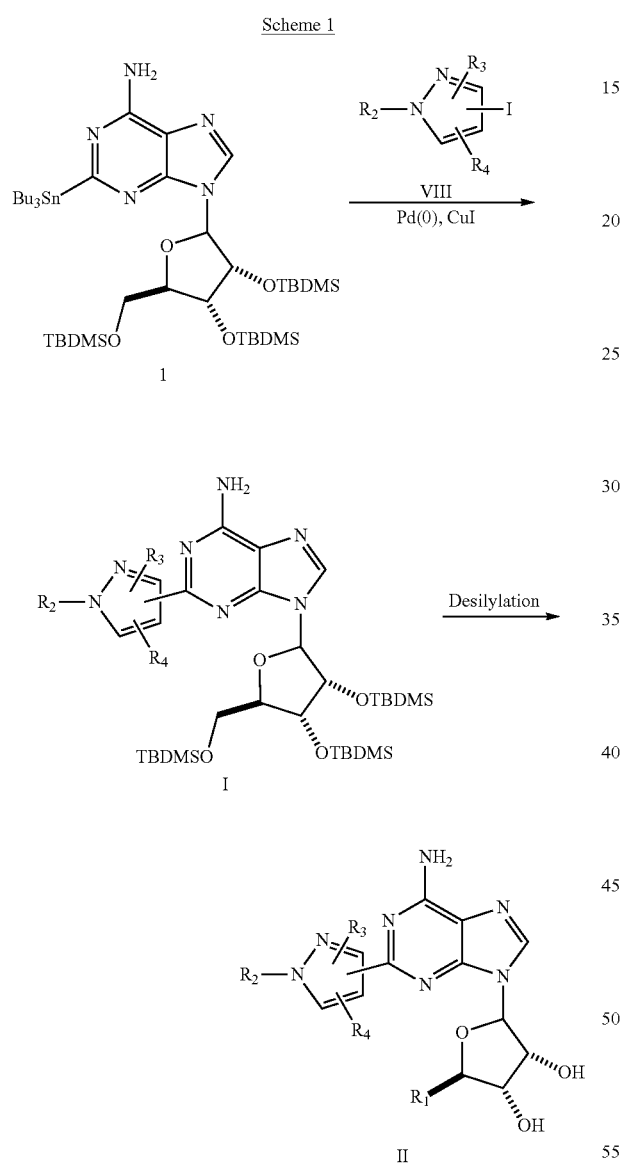

were prepared by the palladium mediated coupling of compound 1 with halo-pyrazoles represented by the formula VIII (scheme 4) in the presence or absence of copper salts (K. Kato et al. J. Org. Chem. 1997, 62, 6833-6841; Palladium Reagents and Catalysts-Innovations in Organic Synthesis, Tsuji, John Wiley and Sons, 1995) followed by de-protection with either TBAF or $NH_4F$ (Markiewicz et al. Tetrahedron Lett. (1988), 29, 1561). The preparation of compound 1 has been previously described (K. Kato et al. J. Org. Chem. 1997, 62, 6833-6841) and is outlined in scheme 7.

Compounds with general formula VI can be prepared as shown in Scheme 2. Compound III, which can be obtained by reacting II with 2,2-dimethoxypropane in presence of an

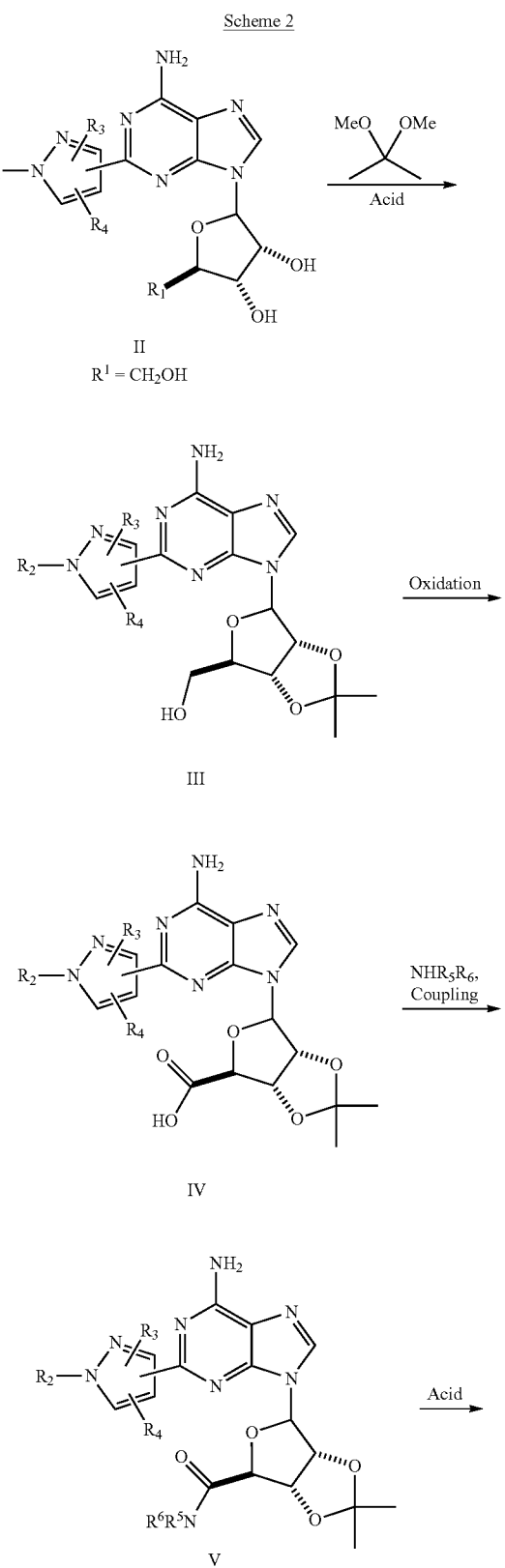

-continued

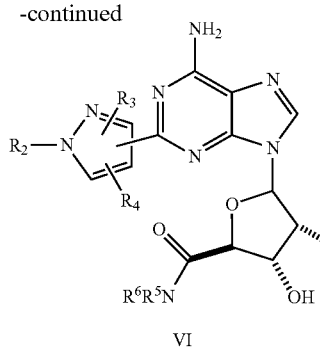

VI acid, can be oxidized to the carboxylic acid IV, based on structurally similar compounds, using potassium permanganate or pyridinium chlorochromate etc. (Jones et al., J. Am. Chem. Soc. (1949), 71, 3994; Hudlicky, Oxidations in organic chemistry, American Chemical Society, Washington D.C., 1990) to compound IV. Reaction of primary or secondary amine of the formula NHR⁵R⁶, and compound IV using DCC (Fujino et al., Chem. Pharm. Bull. (1974), 22, 1857), PyBOP (J. Martinez et al., J. Med. Chem. (1988), 28, 1967) or PyBrop (J. Caste et al. Tetrahedron, (1991), 32, 1967) coupling conditions can afford compound V. Deprotection of compound V can be performed by heating with 80% aq. acetic acid (T. W. Green and P. G. M. Wuts, (1991), Protective Groups in Organic Synthesis, A, Wiley-Interscience publication) or with anhydrous HCl (4N) to obtain compound of the general formula VI.

Alternatively, compounds with the general formula II can also be prepared by Suzuki type coupling as shown in scheme 3.

Scheme 3

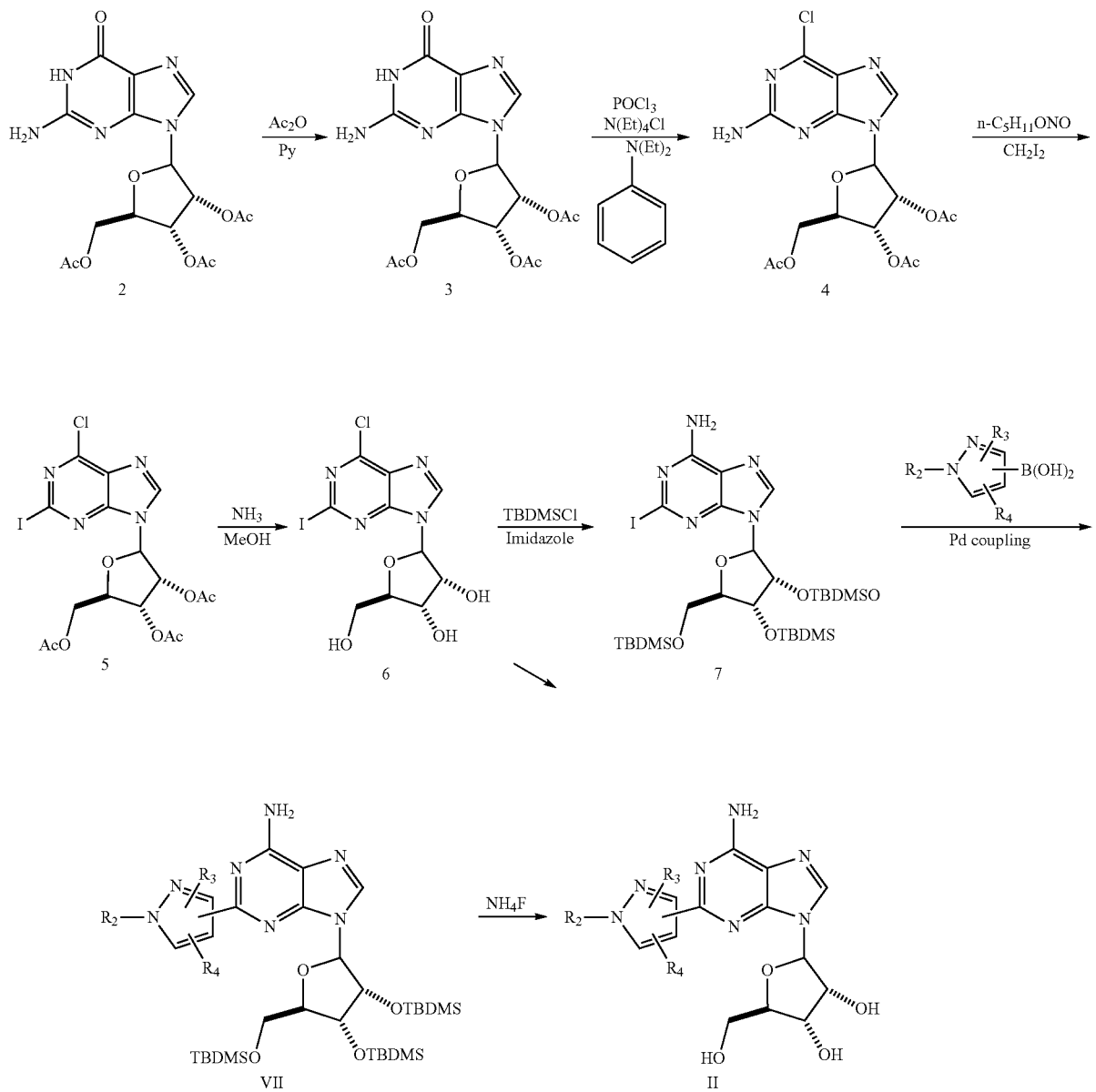

2-Iodoadenosine 6 can be prepared in four steps from guanosine 2 following literature procedures (M. J. Robins et al. Can. J. Chem. (1981), 59, 2601-2607; J. F. Gerster, A. F. Lewis, and R. K. Robins, In Synthetic procedures in nucleic acid chemistry. Vol. 1. Edited by W. W. Zorbach and R. S. Tipson. Wiley-Interscience, New York. 1968. pp. 242-243; V. Nair et al., J. Org. Chem., (1988), 53, 3051-3057). Palladium mediated Suzuki coupling of 6 with appropriately substituted pyrazole-boronic acids XVII in presence of a base can provide final compounds with general formula II (A. Suzuki, Acc. Chem. Res) (1982), 15, 178). If necessary, 2', 3', 5' hydroxyls on 6 can be protected as TBDMS ethers prior to Suzuki coupling.

Compounds with the general formula VIII can be either commercially available or prepared following the steps shown in scheme 4.

Scheme 4

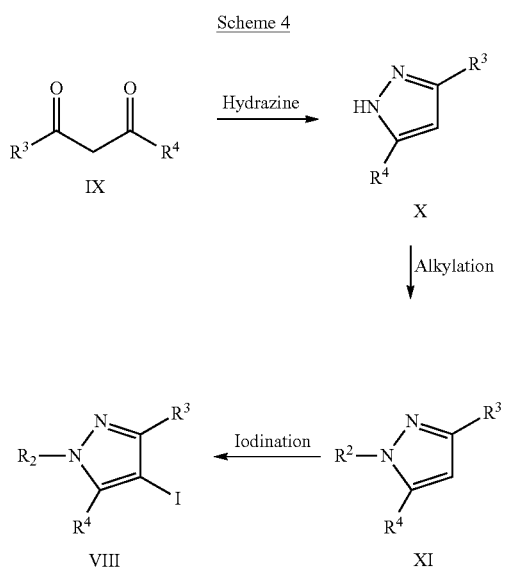

Condensation of 1,3-diketo compounds of the formula IX with hydrazine in an appropriate solvent can give pyrazoles with the general formula X (R. H. Wiley et al. Org. Synthesis, Coll. Vol IV (1963), 351. These pyrazoles can be N-alkylated with various alkyl halides to give compounds of the formula XI which on iodination give 4-iodo derivatives with the general formula VIII (R. Huttel et al. Justus Liebigs Ann. Chem. (1955), 593, 200).

5-iodopyrazoles with the general formula XV can be prepared following the steps outlined in the scheme 5.

Scheme 5

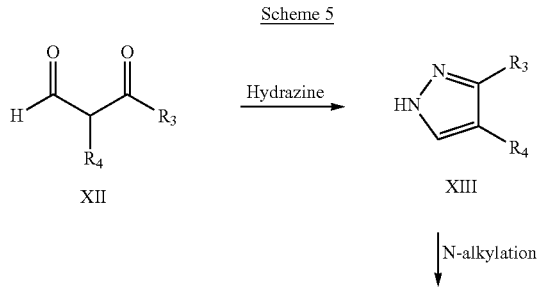

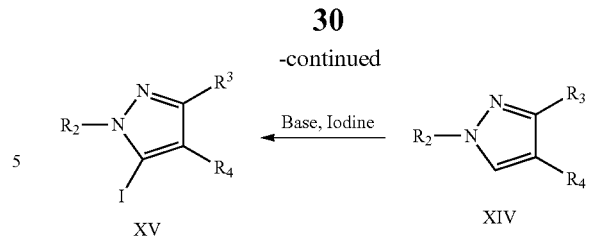

Condensation of 1,3-diketo compounds of the formula XII with hydrazine in an appropriate solvent can give pyrazoles with the general formula XIII. These pyrazoles can be N-alkylated with various alkyl halides to give compounds of the formula XIV. Abstraction of 5-H with a strong base followed by quenching with iodine can provide 5-iodo derivatives with general formula XV (F. Effenberger et al. J. Org. Chem. (1984), 49, 4687).

4- or 5-iodopyrazoles can be transformed into corresponding boronic acids as shown in the scheme 6. Transmetallation with n-buLi followed by treatment with trimethylborate can Scheme 6

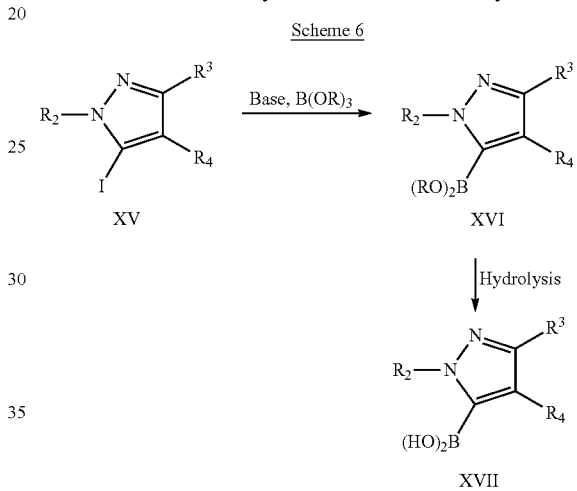

give compounds with the general formula XVI which on hydrolysis can provide boronic acids with the general formula XVII (F. C. Fischer et al. RECUEIL (1965), 84, 439).

2-Stannyladenosine 1 was prepared in three steps from the commercially available 6-chloropurine riboside following literature procedure (K. Kato et al., J. Org. Chem. (1997), 62, 6833-6841). Tri-TBDMS derivative was obtained by treating 8 with TBDMSCl and imidazole in DMF. Lithiation with LTMP followed by quenching with tri n-butyltin chloride gave exclusively 2-stannyl derivative 10. Ammonolysis in 2-propanol gave 2-stannyladenosine 1. Stille coupling of 1 with 1-benzyl-4-iodopyrazole in presence of Pd(PPh$_3$)$_4$ and CuI resulted in 11 (K. Kato et al., J. Org. Chem. (1997), 62, 6833-6841). Deprotection of silyl groups on 2', 3'

Scheme 7

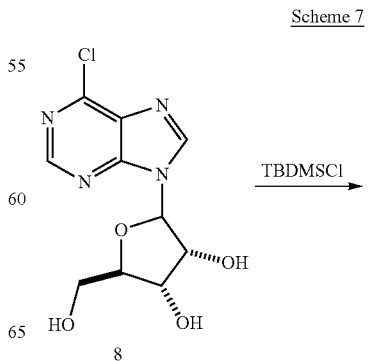

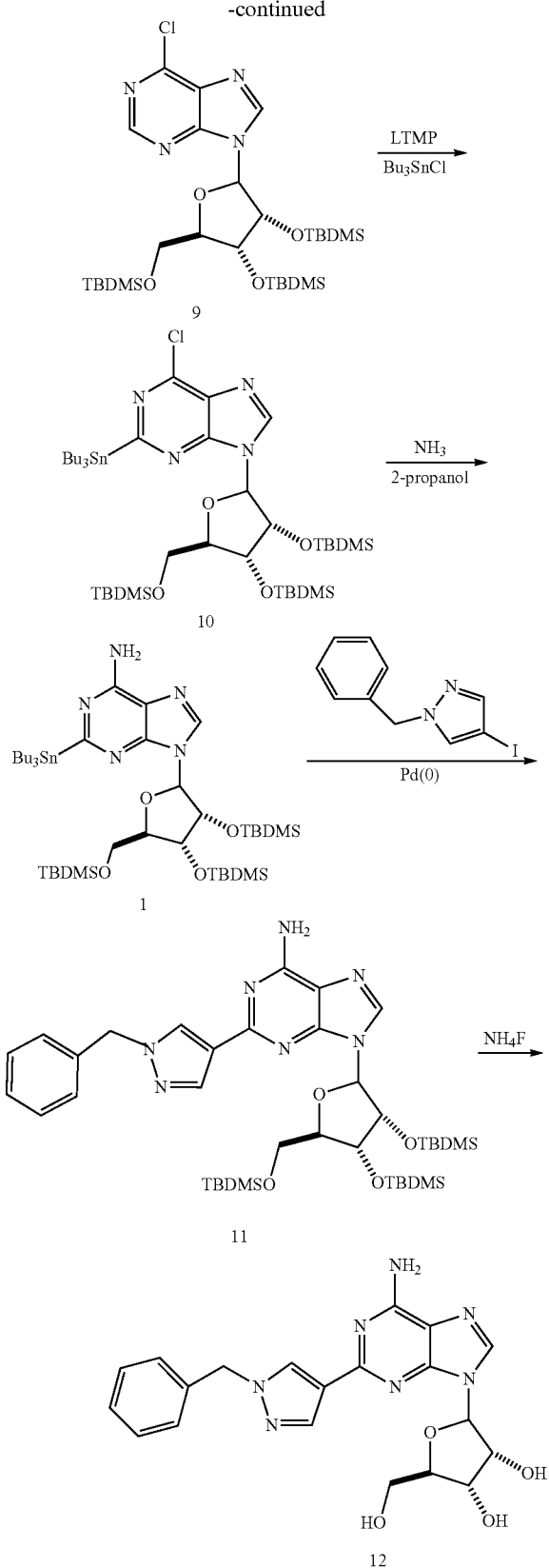

and 5' hydroxyls with 0.5 M ammonium fluoride in methanol gave 12 in good yield (Scheme 7). The methods used to prepare the compounds of this invention are not limited to those described above. Additional methods can be found in the following sources and are included by reference (J. March, Advanced Organic Chemistry; Reaction Mechanisms and Studies (1992), A Wiley Interscience Publications; and J. Tsuji, Palladium reagents and catalysts-Innovations in organic synthesis, John Wiley and Sons, 1995).

If the final compound of this invention contains a basic group, an acid addition salt may be prepared. Acid addition salts of the compounds are prepared in a standard manner in a suitable solvent from the parent compound and an excess of acid, such as hydrochloric, hydrobromic, sulfuric, phosphoric, acetic, maleic, succinic, or methane sulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

EXAMPLES

Three different aqueous pharmaceutical CVT-3146 formulations were used in the Examples below.

Examples 1-7 employed aqueous pharmaceutical compositions (a) and (b) below. Pharmaceutical compositions (a) and (b) were aseptically filled into 10 mL type I glass vials.

(a) An aqueous pharmaceutical composition consisting of 200 micrograms/mL of CVT-3146 in 0.5 (w:v) methylboronic acid buffered with sodium bicarbonate to a pH of 9.3.

(b) An aqueous pharmaceutical composition including 200 micrograms/mL of CVT-3146, 0.1% (w:v) methylboronic acid, 50 mM sodium bicarbonate buffer adjusted to pH 9.3 with the addition of 0.55% (w:v) NaCl to make an isotonic pharmaceutical composition.

Example 8 employed a pharmaceutical composition consisting of an aqueous composition of 100 micrograms/mL CVT-3146 in 15% (w:v) propylene glycol and 100 mM phosphate buffer at pH 7 with 0.1% EDTA. The formulation was stored in type I glass vials at 5 mL per vial.

Example 1

BACKGROUND: CVT-3146, with an initial half-life of 3 minutes with a rapid onset and offset of action, is >100-fold more potent than adenosine (Ado) in increasing coronary blood flow velocity (CBFv) in awake dogs. The purpose of this open label study was to determine the magnitude and duration of effect of CVT-3146 (10-500 µg) on CBFv in humans.

METHODS: Patients undergoing a clinically indicated coronary catheterization with no more than a 70% stenosis in any coronary artery and no more than a 50% stenosis of the study vessel had CBFv determined by Doppler flow wire. Study subject were selected after measuring baseline and peak CBFv after an intracoronary (IC) injection of 18 µg of Ado. Twenty-three patients, who were identified as meeting the study criteria of having a peak to baseline CBFv ratio of ≥2.5 in response to Adenosine, received a rapid (≤10 sec) peripheral IV bolus of CVT-3146; Doppler signals were stable and interpretable over the time-course of the increase in CBFv in 17 patients.

RESULTS: CVT-3146 caused a rapid increase in CBFv that was near peak by 30 to 40 seconds post onset of bolus. CVT-3146 at doses of 100 µg (n=3), 300 µg (n=4), and 500 µg (n=2) induced a peak to baseline ratio of 3.2±0.6 (mean±SD), similar to that obtained by IC Ado (3.2±0.5). The duration of CBFv augmentation (≥2-fold increase in CBFv) was dose dependent; at 300 μg the duration was 4.0±4.9 minutes and at 500 μg was 6.9±7.6 minutes. At 500 μg (n=3) the maximal increase in heart rate (HR) was 18.7±4.0 and the maximal decrease in systolic blood pressure (BP) was 8.7±7.6. Adverse events (AEs) were infrequent and included nausea, flushing, and headache; these were mild and self-limited. No AEs were noted in the 3 patients receiving the 500 μg dose.

CONCLUSION: In humans peak CBFv following CVT-3146 (IV bolus) is comparable to CBFv following IC Ado without major changes in either HR or BP. This agent's magnitude and duration of effect, adverse event profile and bolus administration make CVT-3146 a useful pharmacological stress agent for myocardial perfusion imaging.

Example 2

This example is a study performed to determine the range of dosages over which the selective $A_{2A}$ receptor agonist, CVT-3146 can be administered and be effective as a coronary vasodilator.

The study included patients undergoing a clinically indicated coronary catheterization with no more than a 70% stenosis in any coronary artery and no more than a 50% stenosis of the study vessel had CBFv determined by Doppler flow wire. Study subject were selected after measuring baseline and peak CBFv after an intracoronary (IC) injection of 18 μg of Ado. 36 subjects were identified as meeting the study criteria of having a peak to baseline CBFv ration of ≥2.5 in response to Adenosine, CVT-3146 was administered to the study subjects by IV bolus in less that 10 seconds in amounts ranging from 10 μg to 500 μg.

The effectiveness of both compounds was measured by monitoring coronary flow velocity. Other coronary parameters that were monitored included heart rate and blood pressure. These parameters were measured in order to evaluate the time to peak dose response, the magnitude of the dose response and the duration of the dose response. Adverse events were also monitored. Coronary blood flow velocity was measured at the left anterior descending coronary artery (LAD) or left circumflex coronary artery (LCx). The velocity measurements were taken by following standard heart catheterization techniques and inserting a 0.014 inch Doppler-tipped Flowire into the LAD or LCx vessel and thereafter monitoring blood flow velocity. In addition, hemodynamic and electrocardiographic measurements were recorded continuously.

Overall, 36 human subjects (n=36) were evaluated. Of the 36, 18 were female and 18 were male. Their mean age was 53.4 and they ranged from 24-72 years in age. Of the 36 subjects evaluated, the LAD vessel of 31 subjects was monitored, and the LCx vessel of 5 subjects was monitored. The following doses (μg) of CVT-3146 were given to the subjects in a single iv bolus: 10 (n=4); 30 (n=6); 100 (n=4); 300 (n=7); 400 (n=9); 500 (n=6).

The study results are reported in FIGS. 1-6. The plot of FIG. 1 shows that CVT-3146 increases peak flow velocity in amounts as low as 10 μg and reaches plateau peak velocity upon administration of less than about 100 μg of CVT-3146. Other test results and conclusions include:

The peak flow was reached by about 30 seconds with all doses;

At doses above about 100 μg, peak effects were equivalent to 18 μg adenosine administered IC;

CVT-3146 was generally well tolerated with adverse events being reported in the table attached as FIG. 7;

At 400 μg;

Coronary blood flow velocity ≥2.5-fold above baseline was maintained for 2.8 minutes.

Maximum increase in heart rate (18±8 bpm) occurs about 1 minute after dosing.

Maximum decrease in systolic BP (20±8 mmHg) occurs about 1 minute after dosing.

Maximum decrease in diastolic BP (10±5 mmHg) occurs about 1 minute after dosing.

Example 3

This Example is a study performed to evaluate (1) the maximum tolerated dose of CVT-3146 and (2) the pharmacokinetic profile of CVT-3146 in healthy volunteers, after a single IV bolus dose.

Methods

The study was performed using thirty-six healthy, non-smoking male subjects between the ages of 18 and 59 and within 15% of ideal body weight.

Study Design

The study was performed in phase 1, single center, double-blind, randomized, placebo-controlled, crossover, ascending dose study. Randomization was to CVT-3146 or placebo, in both supine and standing positions.

CVT-3146 was administered as an IV bolus (20 seconds) in ascending doses of 0.1, 0.3, 1.3, 10, 20 and 30 μg/kg.

Subjects received either CVT-3146 of placebo on Day 1 supine, then crossover treatment on Day 2 supine. On Day 3, subjects received CVT-3146 or placebo standing, then crossover treatment on Day 4 standing.

Assessments

Patient safety was monitored by ECG, laboratory assessments, and collection of vital signs and adverse events.

Pharmacokinetics:

Plasma samples were drawn during supine phase (Days 1 and 2) at 0, 1, 2, 3, 4, 5, 7, 10, 15, 20, 30, 45 minutes after dosing and at 1, 1.5, 2, 4, 6, 8, 12 and 24 hours after dosing. Urine was collected for 24 hours for CVT-3146 excretion.

Pharmacodynamics:

The study evaluated the relationship of changes in heart rate to dose in both standing and supine positions and plasma concentration in the supine position. Some of the study results are reported in FIGS. 8-14.

Results

Safety

In general, adverse events reflected the pharmacologic effect of CVT-3146 and were related to vasodilation or an increase in heart rate (HR). Overall, adverse events were short-lived and mild to moderate in severity. There were no serious adverse events. Three events were assessed as severe in intensity. (Table 1).

TABLE 1

Adverse Events labeled as severe in intensity

| | Number of Subjects with AE | |
|---|---|---|
| Event | 20 μg/kg Standing | 30 μg/kg Supine |
| No subjects per group | 4 | 4 |
| Palpitation | 0 | 2 |

TABLE 1-continued

Adverse Events labeled as severe in intensity

| | Number of Subjects with AE | |
|---|---|---|
| Event | 20 µg/kg Standing | 30 µg/kg Supine |
| Dizziness | 1 | 0 |
| Syncope | 1 | 0 |

A three-compartment open model was fit to the data using observed Tmax (1-4 minutes) as the duration of a zero-order infusion. Reliable parameter estimates were obtained for dose of 1-30 µg/kg. Parameters are summarized in the following (Table 2):

TABLE 2

Mean (SD) CVT-3146 Pharmacokinetic Parameters Estimated Using a Three - Compartment Model

| | Dose (µg/kg) | | | | | |
|---|---|---|---|---|---|---|
| | 1 | 3 | 10 | 20 | 30 | Total |
| N | 3 | 4 | 4 | 8 | 3 | 22 |
| CL (mL/min) | 737 (106) | 668 (167) | 841 (120) | 743 (123) | 1021 (92.7) | 768 (168) |
| Vc (L) | 9.84 (4.12) | 13.7 (6.06) | 17.9 (6.11) | 12.5 (5.83) | 15.7 (4.59) | 13.8 (5.67) |
| Vss (L) | 69.0 (28.2) | 90.0 (29.6) | 101 (11.3) | 75.2 (10.6) | 89.6 (10.9) | 75.5 (24.4) |
| α Half-life (min) | 2.14 (1.38) | 3.11 (2.14) | 4.15 (2.75) | 4.69 (4.01) | 3.00 (1.05) | 3.73 (2.88) |
| β Half-life (min) | 8.93 (4.10) | 17.2 (11.4) | 50.2 (52.1) | 32.6 (32.4) | 14.0 (4.98) | 27.2 (31.0) |
| λ Half-life (min) | 99.0 (28.6) | 130 (23.1) | 132 (20.5) | 117 (36.0) | 99.4 (8.10) | 86.4 (57.5) |
| K21 (l/min) | 0.246 (0.255) | 0.203 (0.272) | 0.187 (0.305) | 0.387 (0.615) | 0.0948 (0.0443) | 0.258 (0.410) |
| K31 (l/min) | 0.01808 (0.00548) | 0.0152 (0.00490) | 0.0108 (0.00592) | 0.0141 (0.00728) | 0.0148 (0.000900) | 0.0143 (0.00580) |

CL = clearance
Vc = central volume of distribution
$V_{ss}$ = volume of distribution at steady state
$K_{21}$ = the rate constant for transfer from first peripheral to central compartment
$K_{31}$ = rate constant for transfer from second peripheral to central compartment Results
  CVT-3146 was well-tolerated, with AE's mainly representing its pharmacological effects as an adenosine $A_{2A}$ receptor agonist.
  Mean tolerable dose for CVT-3146 was 10 µg/kg standing and 20 µg/kg supine.
  CVT-3146 does not require weight-adjusted dosing.
  There was no time lag between plasma concentration changes and changes in heart rate.
  The relationship between HR increase and dose or concentration was adequately described with a sigmoidal Emax model.

Example 4

CVT-3146 is a novel selective $A_{2A}$ adenosine receptor agonist being developed as a pharmacologic stressor for radionuclide myocardial perfusion imaging. Previously it has been shown that CVT-3146 causes coronary vasodilation without significantly affecting either total peripheral resistance or renal blood flow in awake dogs. The goal of this study was to determine the differential effects of CVT-3146 on blood flow velocity in various vascular beds.

The effect of CVT-3146 was studied on the blood flow velocity in left circumflex coronary artery (LCX), brain arterial vasculature (BA), forelimb artery (FA) and pulmonary artery (PA) of comparable diameter in the anesthetized dog. CVT-3146 (1.0 µg/kg) was administered as an intravenous bolus, transiently enhanced blood flow which was site specific. The effects of CVT-3146 were quantified as the average peak blood flow velocity (APV) using intravascular Doppler transducer tipped catheter. Heart rate (HR) and systemic arterial blood pressure (BP) were also monitored.

Figure 16:
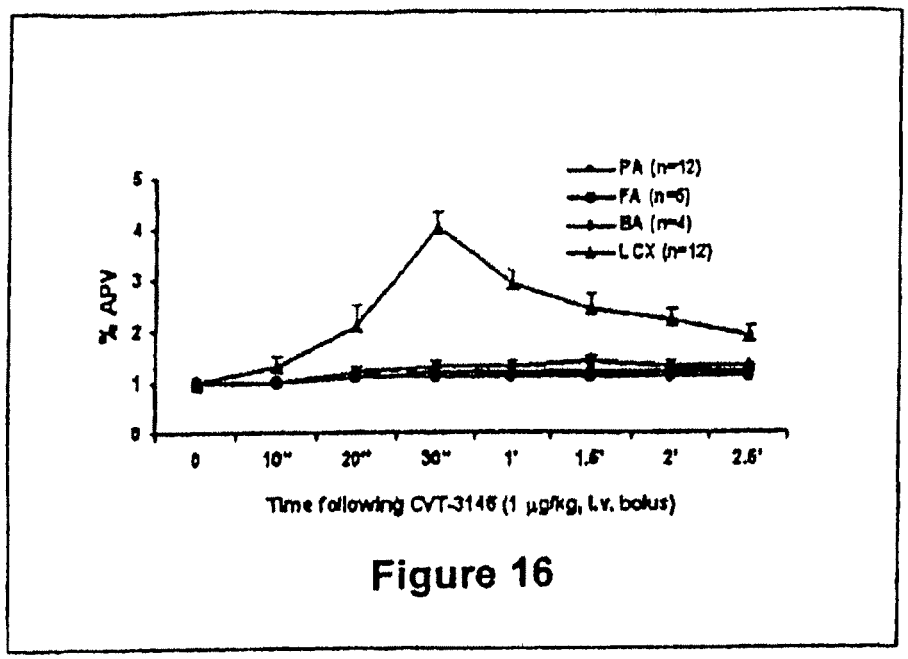
FIG. 16 is a plot of the average peak to blood flow velocity over time following administration of CVT-3146 measured at the pulmonary artery (PA), the four limb artery (FA), brain arterial vasculature (BA) and in the left circumflex coronary artery (LCS)

APV increased 3.1±0.2, 1.4±0.1, 1.2±0.1, and 1.1±0.01 fold in the LCX, BA, FA and PA, respectively manifesting a site-potency rank order of LCX>>BA>FA>PA (FIG. 16). The effect of CVT-3146 on blood flow velocity was short lasting; reaching a peak in less than 30 sec and dissipating in less than ten minutes. Increased blood flow velocity was associated with a small transient increase in HR (16 bpm) and decrease in BP (12 mmHg). In conclusion, this study demonstrated that CVT-3146 is a potent, short lasting vasodilator that is highly selective for the coronary vasculature.

Example 5

The present study was carried out to determine whether CVT-3146, a selective $A_{2A}$ adenosine receptor agonist, causes sympathoexcitation.

Figure 17:
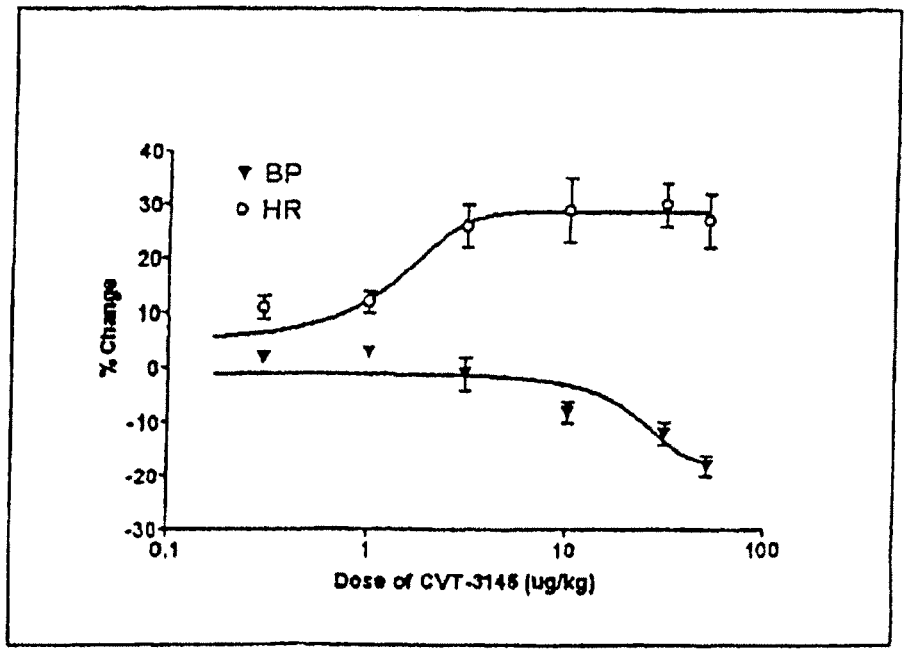
FIG. 17 is a plot of the percent change in heart rate (HR) and blood pressure (BP) for various doses of CVT-3146.

CVT (0.31 µg/kg-50 µg/kg) was given as a rapid i.v. bolus to awake rats and heart rate (HR) and blood pressure (BP) were monitored. CVT-3146 caused an increase in BP and systolic pressure (SP) at lower doses while at higher doses there was a decrease in BP and SP. CVT-3146 caused a dose-dependent increase in HR (FIG. 17). The increase in HR was evident at the lowest dose of CVT at which there was no appreciable decrease in BP. ZM241385 (30 µg/kg, N=5), an $A_{2A}$ receptor antagonist, attenuated the decrease in BP (CVT-3146: 14±3%, ZM: 1±1%) and the increase in HR (CVT: 27±3%, ZM: 18±3%) caused by CVT-3146. Pretreatment with metoprolol (MET, 1 mg/kg, n=5), a beta-blocker, attenuated the increase in HR (CVT: 27±3%, MET: 15±2%), but had no effect on hypotension caused by CVT-3146. In the presence of hexamethonium (HEX, 10 mg/kg, n=5), a ganglionic blocker, the tachycardia was prevented (CVT: 27±3%, HEX: −1±2%), but BP was further reduced (CVT: −11±2%, HEX: −49±5%). CVT-3146 (10 µg/kg, n=6) also significantly (p<0.05) increased plasma norepinephrine (control: 146±11, CVT-3146 269±22 ng/ml) and epinephrine (control:25:f:5, CVT:I00:f:20 ng/ml) levels. The separation of HR and BP effects by dose, time and pharmacological interventions provides evidence that tachycardia caused by CVT-3146 is independent of the decrease in BP, suggesting that CVT-3146, via activation of $A_{2A}$ receptors may cause a direct stimulation of the sympathetic nervous system.

Example 6

Pharmacologic stress SPECT myocardial perfusion imaging (MPI) with adenosine (A) is a well-accepted technique, with excellent diagnostic and prognostic value and proven safety. However, side effects are common and AV nodal block and severe flushing are poorly tolerated. Agents such as CVT-3146 selectively act upon the $A_{2A}$ adenosine receptor and avoid stimulation of other receptor subtypes which may prevent such adverse reactions.

To determine the ability of CVT-3146 to produce coronary hyperemia and accurately detect CAD, 35 subjects (26 men, 9 women; 67±10 years) underwent both A and CVT-3146 stress/rest MPI, with 10.0±9.1 days between studies. Prior MI was noted in 12 patients, and many had prior revascularization [CABG (n=19), PCI (n=22)]. CVT-3146 [400 mcg (n=18), 500 mcg (n=17)] was administered as an IV bolus immediately followed by a saline flush, and then a Tc-99m radiopharmaceutical [sestamibi (n=34), tetrofosmin (n=1)]. SPECT images were uniformly processed, intermixed with control studies (normal and fixed-only defects), and interpreted by three observers in a blinded fashion using a 17-segment model. Quantitative analysis was also performed using 4D MSPECT. In addition to three separate readings, a consensus interpretation was performed and then a direct, same-screen comparison of A and CVT-3146 images undertaken to determine relative differences, using 5 regions per study.

The summed scores following stress were similar, both with visual (A=13.9±1.5, CVT-3146=13.2±1.3; p=n.s.) and quantitative methods of analysis (A=13.7±1.5, CVT-3146=13.6±1.6; p=n.s.). Similarly, comparisons between the summed rest and summed difference scores were identical. The direct comparison also revealed no differences in ischemia detection, with a regional concordance for ischemia extent and severity of 86.3% and 83.4%, respectively. No dose-dependent effect of CVT-3146 on ischemia detection was noted. A conclusion of the study is that CVT-3146, administered by a logistically simple bolus injection, provides a similar ability to detect and quantify myocardial ischemia with SPECT MPI as noted with an A infusion.

Example 7

CVT-3146 is a selective $A_{2A}$ adenosine receptor agonist that produces coronary hyperemia and potentially less adverse effects due to its limited stimulation of receptor subtypes not involved with coronary vasodilation. This study evaluated the effectiveness of CVT-3146 as a pharmacologic stress agent.

36 subjects (27 men, 9 women; 67±10 years) were studied with two doses of CVT-3146 [400 mcg (n=18), 500 mcg (n=18)], administered as an IV bolus, as part of a pharmacologic stress myocardial perfusion imaging protocol.

Adverse effects (AE) occurred in 26 pts (72%), including chest discomfort (33%), headache (25%), and abdominal pain (11%), with a similar incidence for both doses. Flushing, dyspnea, and dizziness were more frequent in the 500-mcg group (44%, 44%, and 28%, respectively) than in the 400-mcg group (17%, 17%, and 11%, respectively). Most AEs were mild to moderate (96%) and resolved within 15 min without treatment (91%). One serious AE occurred, with exacerbation of a migraine headache, which required hospitalization. ST and T wave abnormalities developed with CVT-3146 in 7 and 5 pts, respectively. No 2nd or 3rd degree AV block was noted and there were no serious arrhythmias. Peak hemodynamic effects are shown in Table 3 and were noted at 4 min for systolic blood pressure (BP), 8 min for diastolic BP, and within 2 min for heart rate (HR). The effect on BP was minimal and systolic BP did not fall below 90 mmHg with either dose. The mean change in HR response was higher for the 500 mcg dose (44.2%) than for 400 mcg (34.8%; p=n.s.). Thirty min after CVT-3146, BP changes deviated <2% from baseline but HR remained above baseline by 8.6%.

The results of this study indicate that CVT-3146 is well-tolerated and has acceptable hemodynamic effects. Minimal differences were noted in BP and HR responses between the 400 mcg and 500 mcg doses, but AEs were more frequently at the higher dose. CVT-3146 appears safe and well-tolerated for bolus-mediated pharmacologic stress perfusion imaging. Hemodynamic Changes (mean±S.D.)

TABLE 3

|  | Absolute Change | Relative Change |
| --- | --- | --- |
| Heart Rate | +21.9 ± 10.4 beats per min | +36.7% + 21.0% |
| Systolic BP | −5.9 ± 10.7 mmHg | −4.1% ± 7.6% |
| Diastolic BP | −5.4 ± 7.2 mmHg | −7.9% ± 10.5% |

Example 8

In this study the vasodilator effects of CVT-3146 were compared to those of ADO in different vascular beds in awake dogs. Dogs were chronically instrumented for measurements of the blood flow in coronary (CBF), mesenteric (MBF), hind limb (LBF), and renal (RBF) vascular beds, and hemodynamics. Bolus injections (iv) to CVT-3146 (0.1 to 2.5 μg/kg) and ADO (10 to 250 μg/kg) caused significant increases in CBF (35±6 to 205±23% and 58±13 to 163±16%) and MBF (18±4 to 88±14% and 36±8 to 84±5%).

Figure 18:
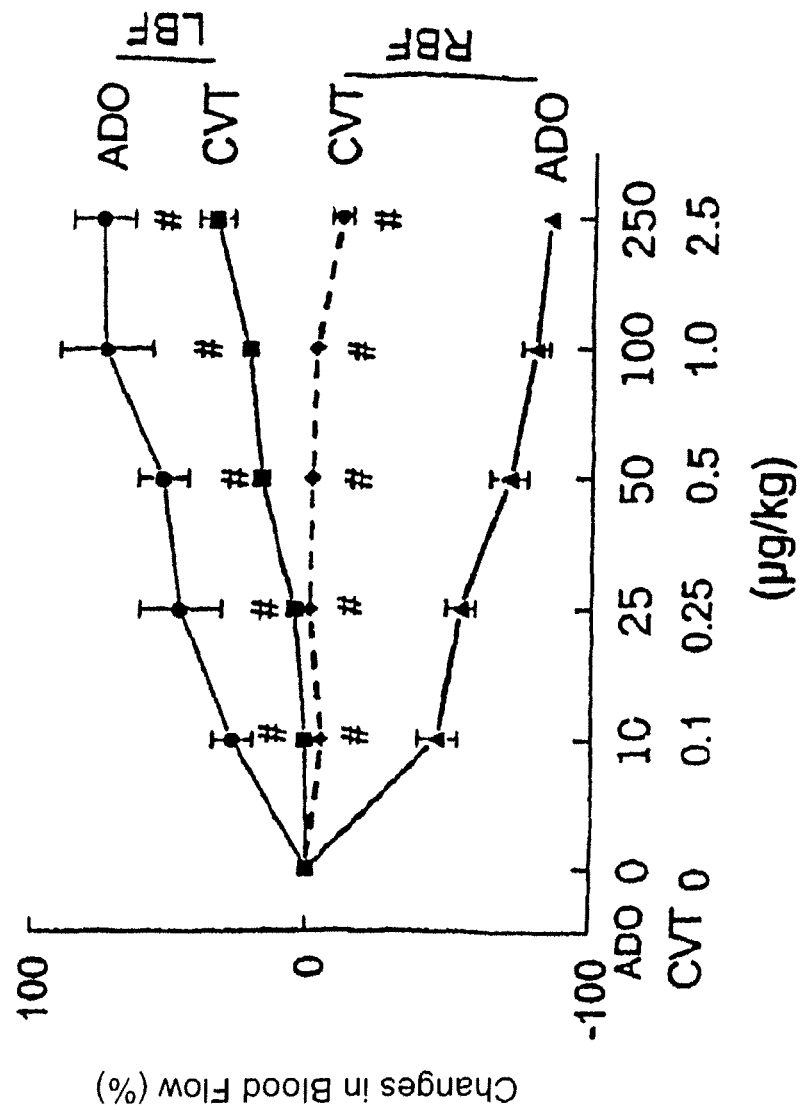
FIG. 18 is a plot of the change in LBF and RBF blood flow upon administering increasing amounts of ADO or CVT-3146 to awake dogs.

The results of the study demonstrate that CVT-3146 is a more potent and longer lasting coronary vasodilator compared to ADO (the duration for CBF above 2-fold of the baseline; CVT-3146 (2.5 μg/kg): 130±19 s; ADO (250 μg/kg): 16±3 s, P<0.5). As shown in FIG. 18 (mean±SE, n=6), CVT-3146 caused a smaller increase in LBF than ADO. ADO caused a dose-dependent renal vasoconstriction (RBF −46±7 to −85±4%), whereas CVT-3146 has no or a little effect on RBF (−5±2 to −11±4%, P<0.05, compared to ADO). In conclusion, CVT-3146 is a more selective and potent coronary vasodilator than ADO. CVT-3146 has no significant effect on renal blood flow in awake dogs. These features of CVT-3146 make it an ideal candidate for radionuclide myocardial perfusion imaging.

The invention now having been fully described, it will be apparent to one of ordinary skill in the art that many changes and modifications can be made thereto without departing from the spirit or scope of the invention.

What is claimed is:

1. A method for myocardial perfusion imaging comprising administering to a human subject in need thereof a compound which has the formula:

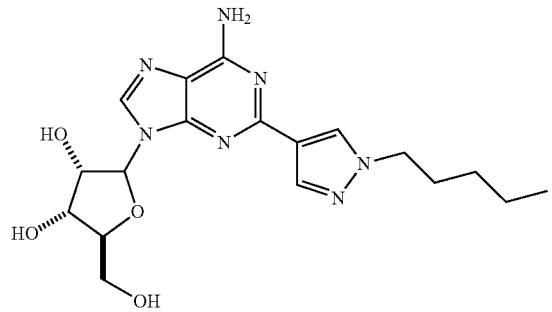 [SMILES: CCCCCn1cc(-c2nc(N)c3ncn(C4O[C@@H](CO)[C@H](O)[C@@H]4O)c3n2)cn1]

with saline and followed by a radionuclide, wherein the myocardium is examined for areas of insufficient blood flow following the administration of the radionuclide.

2. The method of claim 1, wherein the method comprises administering the compound by intravenous (iv) bolus.

3. A method for myocardial perfusion imaging comprising administering a single bolus intravenous injection of a pharmaceutical composition comprising a compound which has the formula:

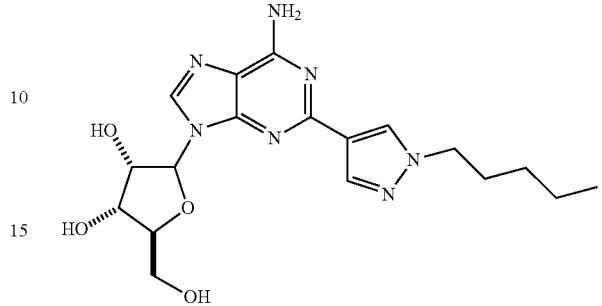

to a human subject in need thereof, wherein the compound is administered in an amount of 10 μg to about 1000 μg, and the amount is independent of the human subject's weight.

* * * * *

UNITED STATES PATENT AND TRADEMARK OFFICE
CERTIFICATE OF CORRECTION

PATENT NO. : 8,906,878 B2  
APPLICATION NO. : 13/848614  
DATED : December 9, 2014  
INVENTOR(S) : Luiz Belardinelli et al.

Page 1 of 1

It is certified that error appears in the above-identified patent and that said Letters Patent is hereby corrected as shown below:

ON THE TITLE PAGE

In Item (57), Abstract, please replace "one $A_{2a}$" with --one $A_{2A}$--.

Signed and Sealed this  
Fifth Day of May, 2015

Michelle K. Lee  
*Director of the United States Patent and Trademark Office*